United States Patent
Addison et al.

(10) Patent No.: US 9,220,440 B2
(45) Date of Patent: Dec. 29, 2015

(54) DETERMINING A CHARACTERISTIC RESPIRATION RATE

(75) Inventors: Paul Stanley Addison, Edinburgh (GB); James Nicholas Watson, Dunfermline (GB); Scott McGonigle, Edinburgh (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 1225 days.

(21) Appl. No.: 12/563,836

(22) Filed: Sep. 21, 2009

(65) Prior Publication Data
US 2011/0071406 A1 Mar. 24, 2011

(51) Int. Cl.
*A61B 5/08* (2006.01)
*A61B 5/0205* (2006.01)
(Continued)

(52) U.S. Cl.
CPC .............. *A61B 5/0816* (2013.01); *A61B 5/0205* (2013.01); *A61B 5/1455* (2013.01); *A61B 5/165* (2013.01); *A61B 5/726* (2013.01); *A61B 5/7278* (2013.01); *A61B 5/7203* (2013.01); *A61B 7/003* (2013.01)

(58) Field of Classification Search
CPC .... A61B 5/0816; A61B 5/1455; A61B 5/165; A61B 5/726; A61B 5/0205; A61B 5/7278; A61B 5/7203; A61B 7/003; A61B 5/021; A61B 5/026
USPC ................ 600/483, 484, 300, 301, 529, 538; 607/6, 9, 20, 23, 25
See application file for complete search history.

(56) References Cited

U.S. PATENT DOCUMENTS

| 3,835,840 A | 9/1974 | Mount |
| 4,561,447 A | 12/1985 | Kawamura et al. |

(Continued)

FOREIGN PATENT DOCUMENTS

| EP | 0443267 | 8/1991 |
| EP | 0755221 | 1/1997 |

(Continued)

OTHER PUBLICATIONS

Mancia et al., Alerting Reaction and Rise in Blood Pressure During Measurement by Physician and Nurse, Feb. 1987, Hypertension, vol. 9(2), pp. 209-215.*

(Continued)

*Primary Examiner* — Michael Kahelin
*Assistant Examiner* — Tho Tran
(74) *Attorney, Agent, or Firm* — Shvarts & Leiz LLP

(57) ABSTRACT

The present disclosure relates to monitoring a characteristic respiration rate of a patient based at least in part on a suitable time period that either precedes or follows a triggering event, such as a clinician/patient interaction, where the triggering event may negatively impact the physiological parameter. In some embodiments, physiological parameter values falling between one or more pre-set thresholds may be used to derive the characteristic physiological parameter. In some embodiments, monitoring the respiration rate may provide additional information about the patient's status. In some embodiments, confidence measures may be associated with, or may be used to analyze features of the patient signal to derive information about, the characteristic respiration rate. The patient signal used to derive a patient's respiration rate may be of an oscillatory nature or may include oscillatory features that may be analyzed to derive a characteristic respiration rate.

20 Claims, 17 Drawing Sheets

(51) Int. Cl.
*A61B 5/1455* (2006.01)
*A61B 5/16* (2006.01)
*A61B 7/00* (2006.01)
*A61B 5/00* (2006.01)

(56) References Cited

U.S. PATENT DOCUMENTS

| | | |
|---|---|---|
| 4,676,253 A | 6/1987 | Newman |
| 4,729,382 A | 3/1988 | Schaffer |
| 4,830,017 A | 5/1989 | Perry |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle |
| 5,065,765 A | 11/1991 | Eckerle |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada |
| 5,163,328 A | 11/1992 | Holland |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,190,038 A * | 3/1993 | Polson et al. ............... 600/330 |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,431,159 A | 7/1995 | Baker |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan |
| 5,617,868 A | 4/1997 | Harada |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa |
| 5,682,898 A | 11/1997 | Aung |
| 5,685,316 A | 11/1997 | Schookin et al. |
| 5,704,362 A | 1/1998 | Hersh et al. |
| 5,709,212 A | 1/1998 | Sugo |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu |
| 5,772,601 A | 6/1998 | Oka |
| 5,772,602 A | 6/1998 | Sakai |
| 5,776,071 A | 7/1998 | Inukai |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias |
| 5,830,131 A | 11/1998 | Caro et al. |
| 5,832,924 A | 11/1998 | Archibald et al. |
| 5,833,618 A | 11/1998 | Caro |
| 5,848,970 A | 12/1998 | Voss |
| 5,857,975 A | 1/1999 | Golub |
| 5,873,834 A | 2/1999 | Yanagi et al. |
| 5,904,654 A | 5/1999 | Wohltmann et al. |
| 5,941,828 A | 8/1999 | Archibald et al. |
| 5,964,711 A | 10/1999 | Voss |
| 6,002,952 A | 12/1999 | Diab |
| 6,004,274 A | 12/1999 | Nolan |
| 6,007,492 A | 12/1999 | Goto et al. |
| 6,011,986 A | 1/2000 | Diab et al. |
| 6,022,320 A | 2/2000 | Ogura |
| 6,027,452 A | 2/2000 | Flaherty et al. |
| 6,027,453 A | 2/2000 | Miwa |
| 6,027,455 A | 2/2000 | Inukai et al. |
| 6,045,509 A | 4/2000 | Caro et al. |
| 6,067,462 A | 5/2000 | Diab |
| 6,083,171 A | 7/2000 | Ono et al. |
| 6,095,987 A | 8/2000 | Shmulewitz |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace |
| 6,293,915 B1 | 9/2001 | Amano et al. |
| 6,299,582 B1 | 10/2001 | Brockway et al. |
| 6,332,867 B1 | 12/2001 | Chen et al. |
| 6,350,242 B1 | 2/2002 | Doten et al. |
| 6,371,921 B1 | 4/2002 | Caro |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,986 B2 | 5/2003 | Baura |
| 6,589,185 B1 | 7/2003 | Archibald et al. |
| 6,599,251 B2 | 7/2003 | Chen et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,626,839 B2 | 9/2003 | Doten et al. |
| 6,631,281 B1 | 10/2003 | Kastle |
| 6,645,156 B2 | 11/2003 | Oka |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab |
| 6,767,328 B2 | 7/2004 | Kulik |
| 6,773,397 B2 | 8/2004 | Kelly |
| 6,783,498 B2 | 8/2004 | Sackner |
| 6,816,741 B2 | 11/2004 | Diab |
| 6,822,564 B2 | 11/2004 | Al-Ali |
| 6,826,419 B2 | 11/2004 | Diab |
| 6,827,688 B2 | 12/2004 | Goto et al. |
| 6,852,083 B2 | 2/2005 | Caro |
| 6,855,112 B2 | 2/2005 | Kao |
| 6,863,652 B2 | 3/2005 | Huang et al. |
| 6,869,403 B2 | 3/2005 | Narimatsu et al. |
| 6,929,610 B2 | 8/2005 | Forstner |
| 6,996,427 B2 | 2/2006 | Ali et al. |
| 7,004,907 B2 | 2/2006 | Banet |
| 7,030,749 B2 | 4/2006 | Al-Ali |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |

(56) References Cited

U.S. PATENT DOCUMENTS

| | | | |
|---|---|---|---|
| 7,079,035 B2 | 7/2006 | Bock et al. | |
| 7,087,025 B2 | 8/2006 | Baruch | |
| 7,184,809 B1 | 2/2007 | Sterling | |
| 7,215,984 B2 | 5/2007 | Diab et al. | |
| 7,215,986 B2 | 5/2007 | Diab et al. | |
| 7,252,636 B2 | 8/2007 | Brown | |
| 7,320,030 B2 | 1/2008 | Brown | |
| 7,335,162 B2 | 2/2008 | Eide | |
| 7,355,512 B1 | 4/2008 | Al-Ali | |
| 7,376,238 B1 | 5/2008 | Rivas et al. | |
| 7,390,300 B2 | 6/2008 | Inukai | |
| 7,390,301 B2 | 6/2008 | Skrabal | |
| 7,393,327 B2 | 7/2008 | Inukai | |
| 7,400,257 B2 | 7/2008 | Rivas | |
| 7,455,643 B1 | 11/2008 | Li et al. | |
| 7,481,772 B2 | 1/2009 | Banet | |
| 7,485,095 B2 | 2/2009 | Shusterman | |
| 7,725,187 B1 * | 5/2010 | Nabutovsky et al. | 607/19 |
| 2003/0060721 A1 * | 3/2003 | Nakazawa et al. | 600/490 |
| 2003/0078619 A1 * | 4/2003 | Bonnet et al. | 607/4 |
| 2003/0139780 A1 * | 7/2003 | Markowitz et al. | 607/17 |
| 2004/0152956 A1 * | 8/2004 | Korman | 600/300 |
| 2004/0242979 A1 * | 12/2004 | Kawasaki | 600/323 |
| 2005/0119866 A1 * | 6/2005 | Zaleski | 702/189 |
| 2005/0148885 A1 | 7/2005 | Tweed et al. | |
| 2005/0251344 A1 | 11/2005 | Appel et al. | |
| 2005/0261594 A1 | 11/2005 | Banet | |
| 2006/0009700 A1 | 1/2006 | Brumfield et al. | |
| 2006/0063992 A1 | 3/2006 | Yu et al. | |
| 2006/0063993 A1 | 3/2006 | Yu et al. | |
| 2006/0079945 A1 | 4/2006 | Libbus | |
| 2006/0206021 A1 | 9/2006 | Diab | |
| 2006/0211925 A1 | 9/2006 | Lamego et al. | |
| 2006/0217614 A1 | 9/2006 | Takala et al. | |
| 2006/0217628 A1 | 9/2006 | Huiku | |
| 2006/0241975 A1 | 10/2006 | Brown | |
| 2006/0285736 A1 | 12/2006 | Brown | |
| 2006/0287603 A1 | 12/2006 | Bartnik et al. | |
| 2007/0066910 A1 | 3/2007 | Inukai et al. | |
| 2007/0083093 A1 | 4/2007 | Diab | |
| 2007/0118045 A1 | 5/2007 | Naghavi et al. | |
| 2007/0135725 A1 * | 6/2007 | Hatlestad | 600/529 |
| 2007/0225582 A1 | 9/2007 | Diab et al. | |
| 2007/0249467 A1 | 10/2007 | Hong et al. | |
| 2008/0015451 A1 | 1/2008 | Hatib et al. | |
| 2008/0030468 A1 | 2/2008 | Ali et al. | |
| 2008/0033305 A1 | 2/2008 | Hatib et al. | |
| 2008/0076991 A1 * | 3/2008 | Ayers et al. | 600/324 |
| 2008/0132798 A1 | 6/2008 | Hong et al. | |
| 2008/0139955 A1 * | 6/2008 | Hansmann et al. | 600/529 |
| 2008/0146890 A1 * | 6/2008 | LeBoeuf et al. | 600/300 |
| 2008/0214903 A1 | 9/2008 | Orbach | |
| 2008/0214942 A1 | 9/2008 | Oh et al. | |
| 2008/0242955 A1 | 10/2008 | Uutela et al. | |
| 2009/0048497 A1 | 2/2009 | Keren | |
| 2009/0118626 A1 * | 5/2009 | Moon et al. | 600/484 |
| 2010/0280395 A1 * | 11/2010 | Lin | 600/485 |
| 2010/0331724 A1 * | 12/2010 | Watson et al. | 600/561 |

FOREIGN PATENT DOCUMENTS

| | | | |
|---|---|---|---|
| GB | 2 356 250 | 5/2001 | |
| GB | 2 356 251 | 5/2001 | |
| GB | 2 356 252 | 5/2001 | |
| JP | 03-231630 | 10/1991 | |
| JP | 06-142082 | 5/1994 | |
| JP | 07-136136 | 5/1995 | |
| JP | 03-225268 | 12/2003 | |
| KR | 2006081166 * | 7/2006 | H04B 1/40 |
| WO | WO 2007018921 A2 * | 2/2007 | A61B 5/00 |

OTHER PUBLICATIONS

Addison, Paul S., The Illustrated Wavelet Transform Handbook, Taylor & Francis Group, 2002.

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

Berne, Robert M., Levy, Matthew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

* cited by examiner

DETERMINING A CHARACTERISTIC RESPIRATION RATE

SUMMARY

The present disclosure relates to patient monitoring, and more particularly, relates to determining a characteristic, or representative, physiological parameter of a patient.

It may be important to monitor certain physiological parameters of a patient, such as respiration rate and blood pressure, in a clinical setting. For example, information about a patient's true or characteristic respiration rate (i.e., the patient's respiration rate at rest and in the absence of distraction, movement, or distress) may be important for diagnosing and/or monitoring the progress of pneumonia or another physiological ailment. One or more of the patient's physiological parameters may be distinctly altered, however, if the patient is aware that he or she is being monitored, resulting in one or more physiological parameter values being reported or displayed that is not the characteristic value. It may therefore be clinically important to report a characteristic physiological parameter value that is not affected by or altered as a result of the patient's interaction with the clinician (i.e., the characteristic respiration rate or characteristic blood pressure).

In an embodiment, the characteristic respiration rate may be obtained from analyzing the patient's respiration rate from any suitably defined time period preceding a triggering event (i.e., the patient's interaction with the clinician) that affects or alters the patient's respiration rate. For example, the average respiration rate, the median respiration rate, the mode respiration rate, or a weighted average or an average obtained without using outlier data may be used to derive the characteristic respiration rate. In some embodiments, respiration rate values or respiration rate slope values falling between one or more pre-set thresholds may be used to derive the characteristic respiration rate. In an embodiment, one or more confidence measures may be used in deriving the reported characteristic respiration rate.

In an embodiment, the characteristic blood pressure may be obtained from analyzing the patient's blood pressure following a triggering event (i.e., the patient's interaction with the clinician) that affects or alters the patient's blood pressure. In some embodiments, the change in the patients blood pressure may be used to examine patient anxiety. In some embodiments, a characteristic blood pressure value may be reported with an associated high or low confidence.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
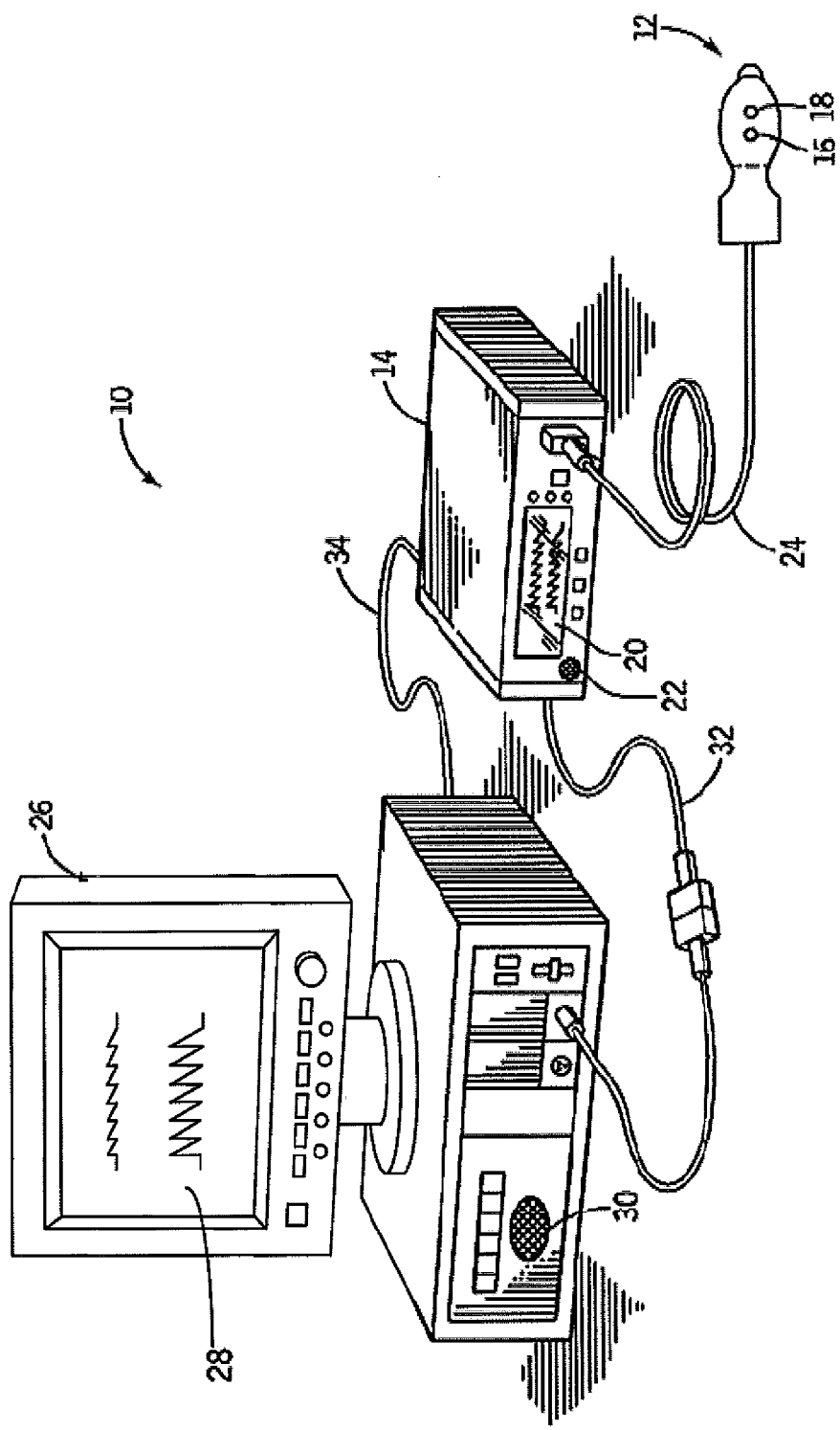
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t) = I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{\frac{dI}{dt}}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} = \frac{\left[I(t_2,\lambda_R)-I(t_1,\lambda_R)\right]I(t_1,\lambda_{IR})}{\left[I(t_2,\lambda_{IR})-I(t_1,\lambda_{IR})\right]I(t_1,\lambda_R)} = R \quad (7)$$

which defines a cluster of points whose slope of y versus x will give R where $x(t)=[I(t_2,\lambda_{IR})-I(t_1,\lambda_{IR})]I(t_1,\lambda_R)$ $y(t)=[I(t_2,\lambda_R)-I(t_1,\lambda_R)]I(t_1,\lambda_{IR})$ $y(t)=Rx(t) \quad (8)$ FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD)

sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "$SpO_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
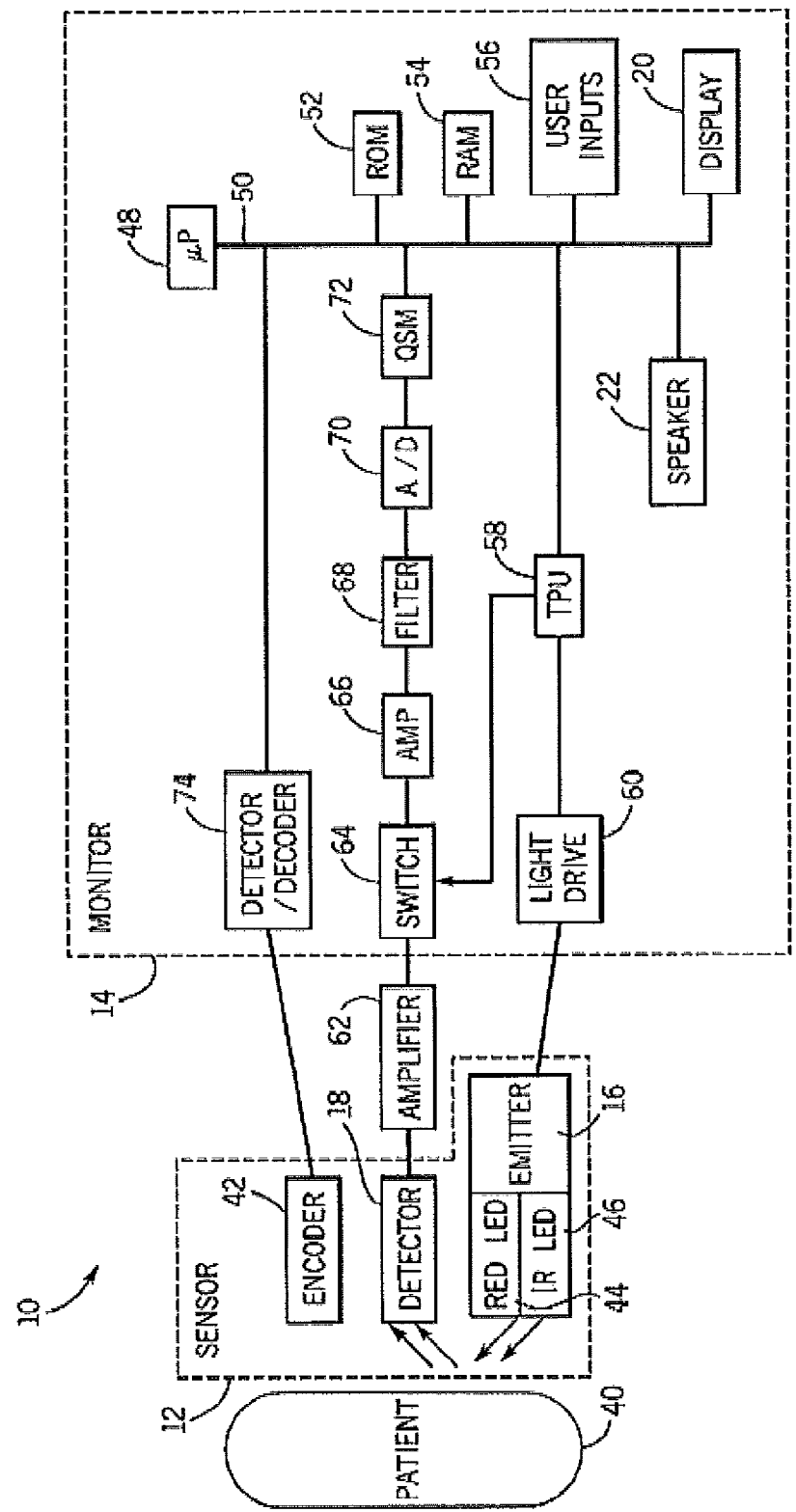
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as SpO₂ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a,b) = \frac{1}{\sqrt{a}} \int_{-\infty}^{+\infty} x(t)\psi^*\left(\frac{t-b}{a}\right)dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \quad (10)$$

where '||' is the modulus operator. The scalogram may be rescaled for useful purposes. One common rescaling is defined as $$S_R(a, b) = \frac{|T(a, b)|^2}{a} \quad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unsealed wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
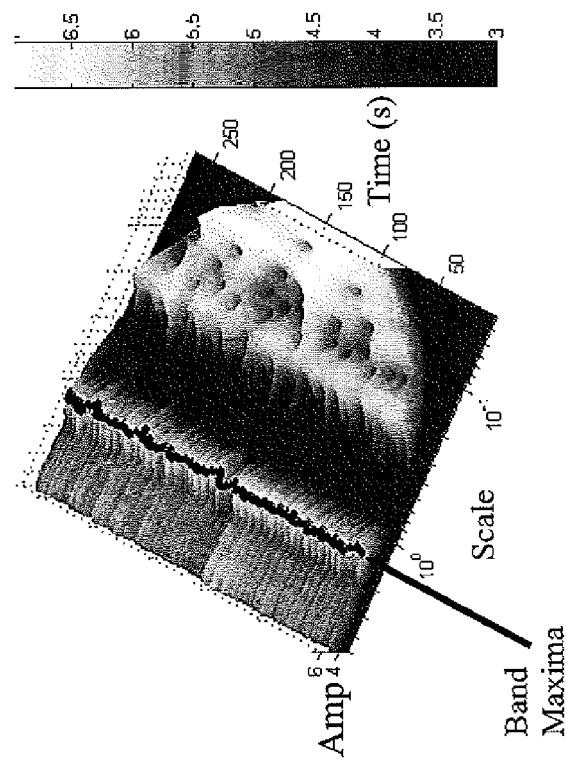
FIGS. 3(a) and 3(b) show illustrative views of a scalogram derived from a PPG signal in accordance with an embodiment.
Figure 3A:
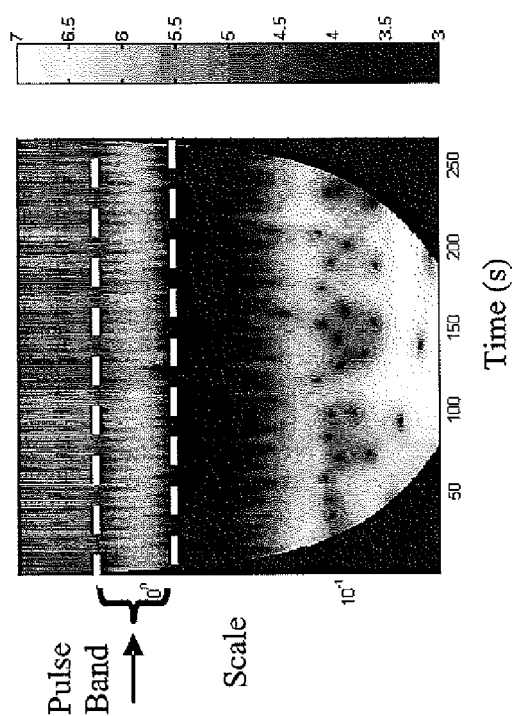

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
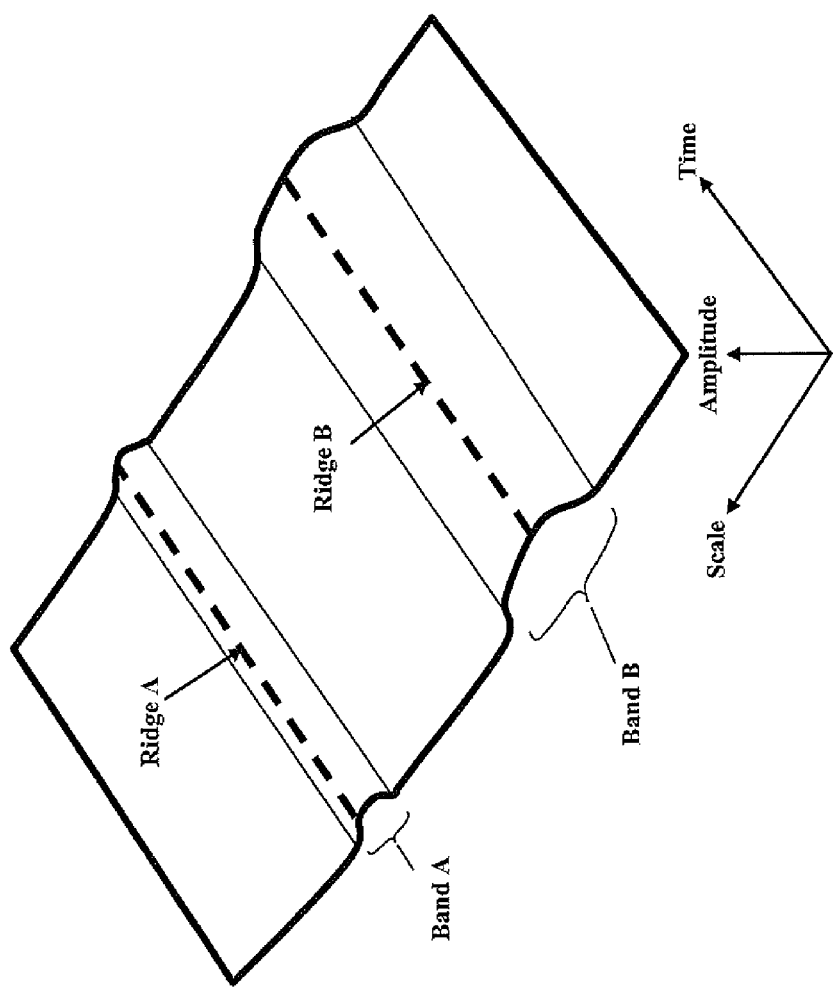
FIG. 3(c) shows an illustrative scalogram derived from a signal containing two pertinent components in accordance with an embodiment.
Figure 3D:
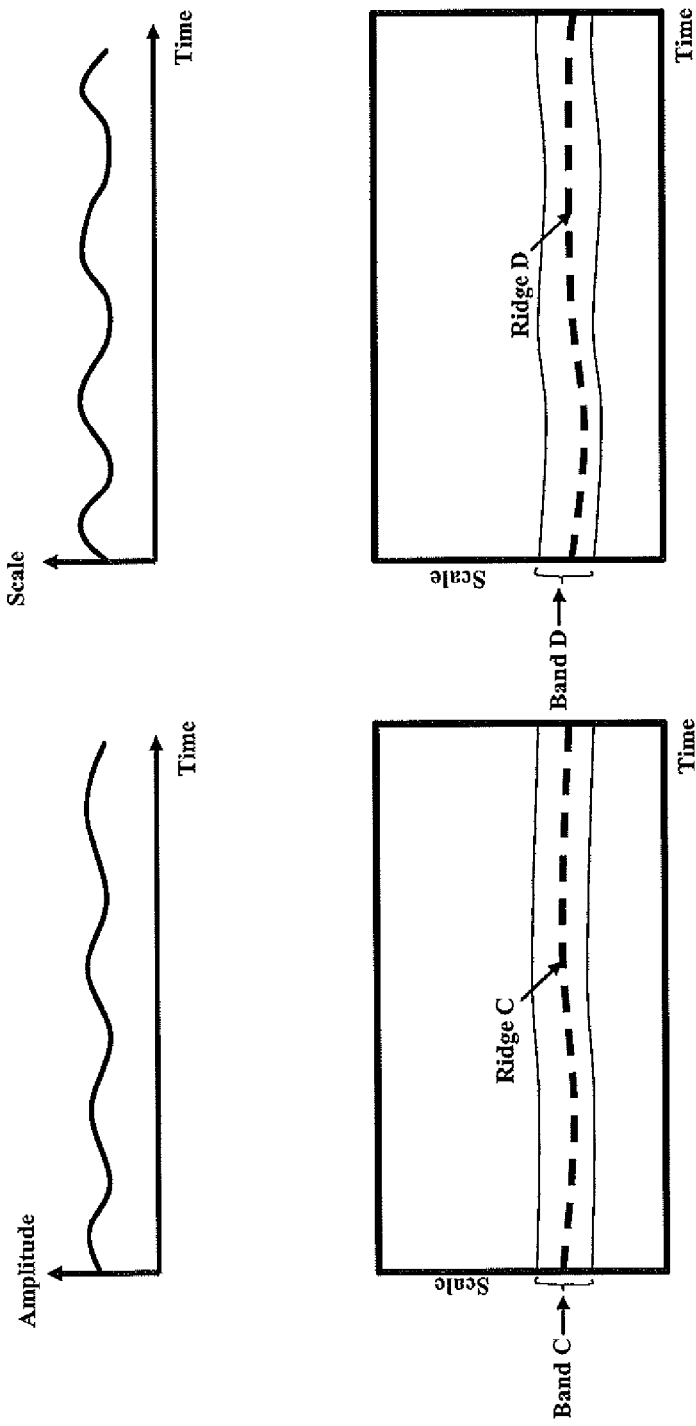
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_{0}^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_{0}^{\infty} T(a,b) \psi_{a,b}(f) \frac{da\,db}{a^2} \quad (16)$$

where $C_g$ is a scalar value known as the admissibility constant. It is wavelet type dependent and may be calculated from:

$$C_g = \int_{0}^{\infty} \frac{|\hat{\psi}(f)|^2}{f} df \quad (17)$$

Figure 3E:
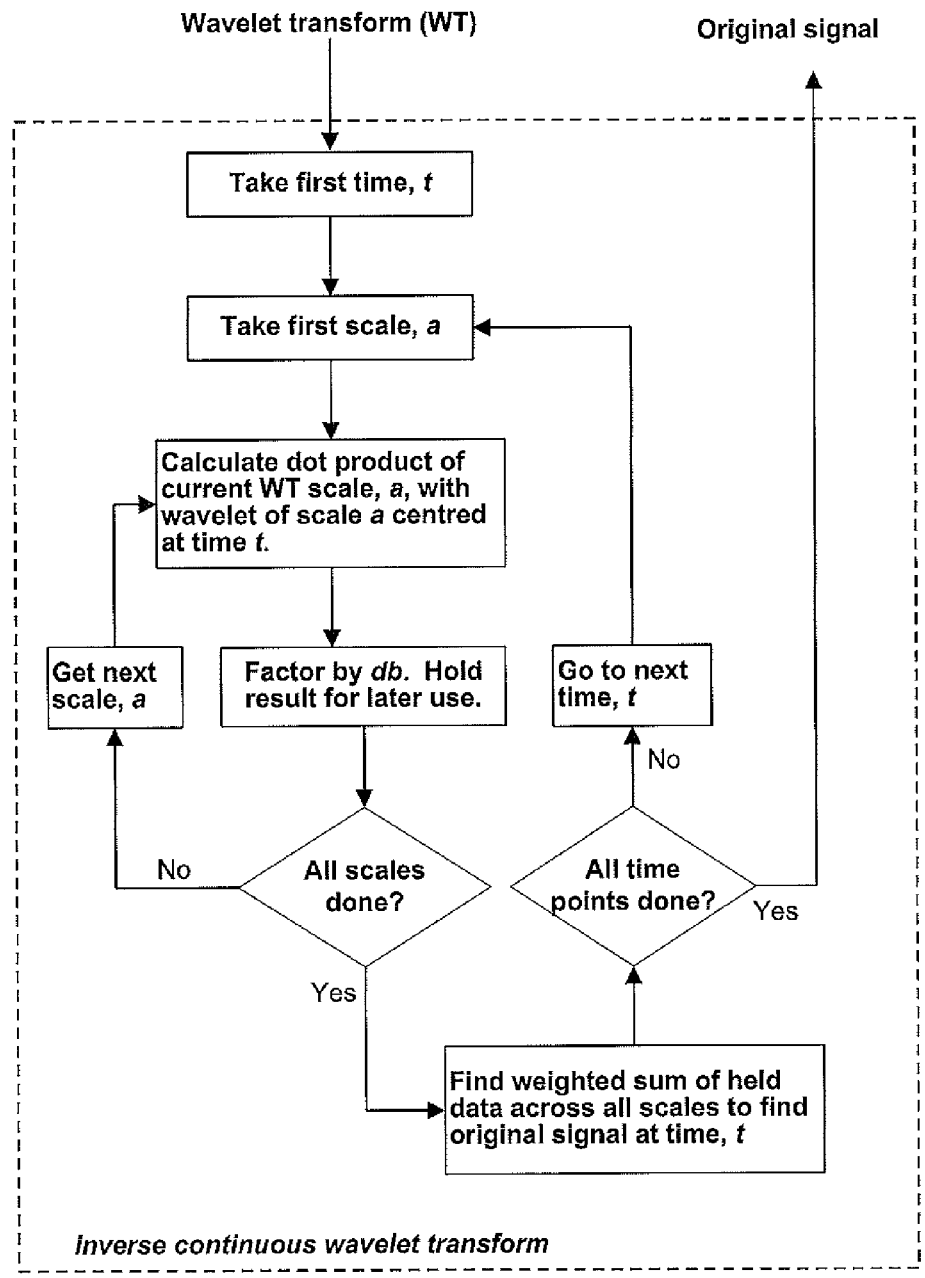
FIGS. 3(e) and 3(f) are flow charts of illustrative steps involved in performing an inverse continuous wavelet transform in accordance with embodiments.
Figure 3F:
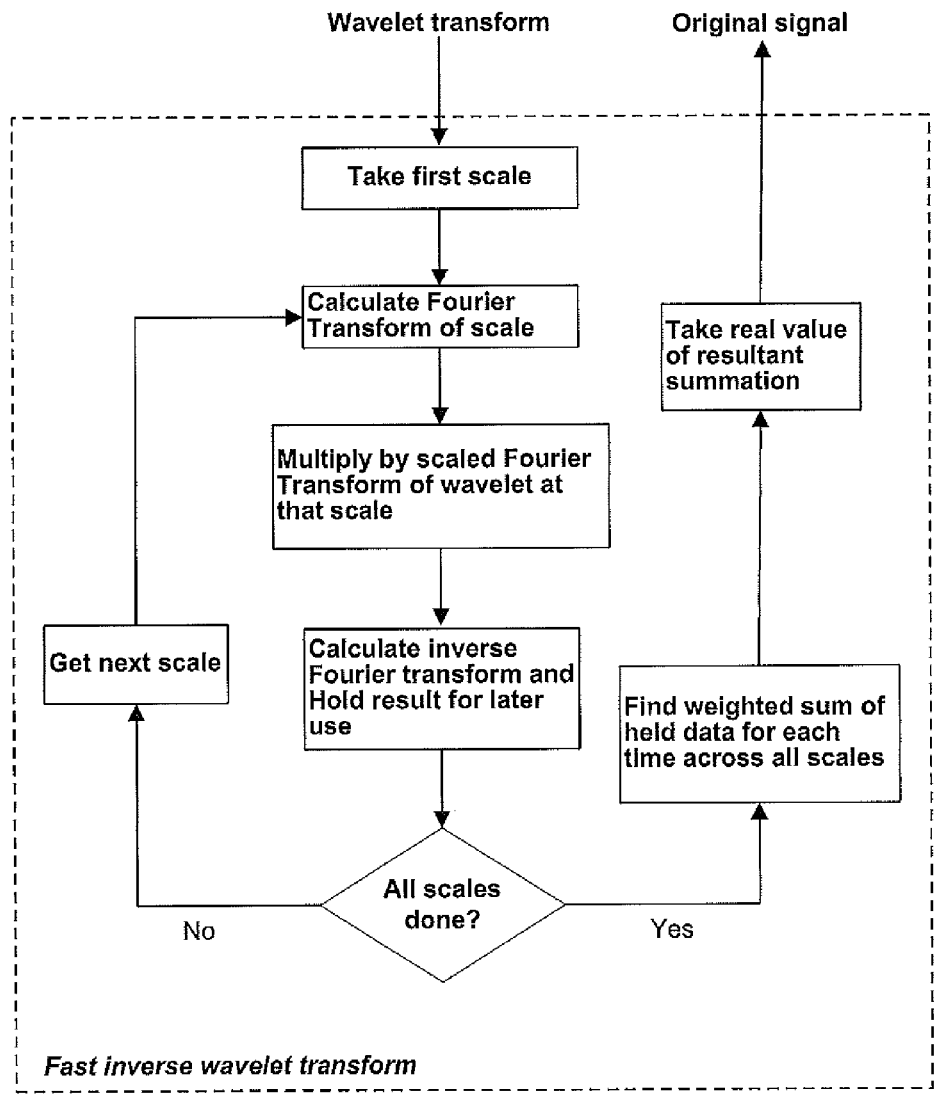

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
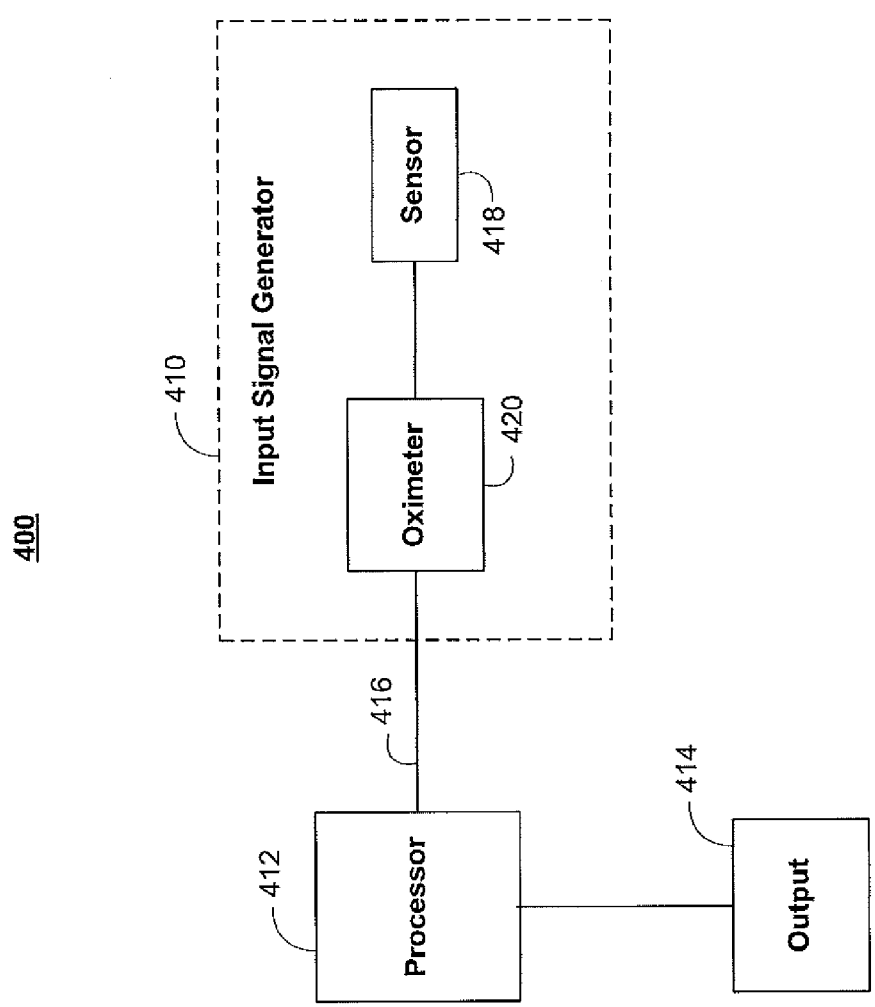
FIG. 4 is a block diagram of an illustrative continuous wavelet processing system in accordance with some embodiments.

FIG. 4 is an illustrative continuous wavelet processing system 400 in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14. It will be further understood that system 400 and/or system 10 may be adapted to derive from any other suitable signal sensed from a patient (i.e., patient 40) any other suitable physiological parameters, such as respiration rate and blood pressure. For example, microprocessor 48 may determine the patient's respiration rate and/or blood pressure using various algorithms and/or look-up tables based on the value of the received signals and/or data corresponding to the light received by detector 18.

It may be important to monitor certain physiological parameters of a patient, such as respiration rate and blood pressure, in a clinical setting. For example, respiration rate information may be important for diagnosing and/or monitoring the progress of pneumonia or another physiological ailment. Blood pressure information may be important for diagnosing or monitoring a cardiovascular ailment. The patient's physiological parameters may be affected, however, if the patient is aware that one or more of the physiological parameters is being monitored. It may therefore be clinically important to report a characteristic physiological parameter (i.e., the patient's respiration rate and/or blood pressure at rest and in the absence of distraction, movement, or distress) that is not affected by or altered as a result of a triggering event, such as a patient's interaction with the clinician. In an embodiment, the characteristic respiration rate may be obtained from analyzing the patient's respiration rate from any suitably defined time period preceding a triggering event. In an embodiment, the characteristic blood pressure may be obtained from analyzing the patient's blood pressure following a last or most recent triggering event. In an embodiment, confidence measures may be associated with the reported characteristic physiological parameters. It will be understood that the present disclosure may be applied to any suitable physiological parameter (i.e., respiration rate, blood pressure, blood oxygen saturation) and may be used to determine a characteristic value of that physiological parameter. However, for brevity and clarity, certain embodiments may be described in terms of respiration rate, blood pressure, or both, below. Embodiments will now be discussed in connection with FIGS. 5-13.

Figure 5:
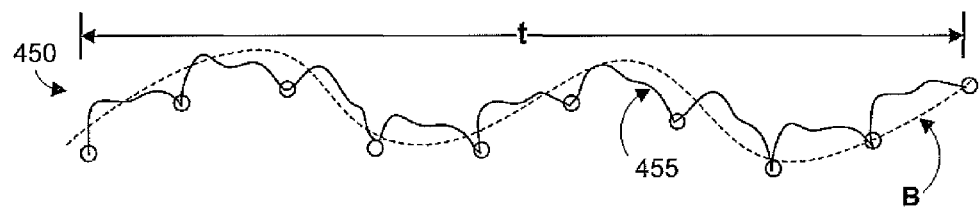
FIG. 5 shows an illustrative PPG signal obtained from a patient in accordance with an embodiment.

The respiration rate of a patient may be derived from any suitable signal using, for example, system 10 or system 400. FIG. 5 shows an illustrative PPG signal 450 obtained from a patient over time period t in accordance with an embodiment. In an embodiment, signal 450 may be of an oscillatory nature due to the patient's breathing (e.g., the baseline of signal 450 may oscillate in relation to the patient's breathing as shown by baseline B) and may include other oscillatory features (e.g., may contain repeating oscillatory pulses like pulse 455) that may be analyzed to derive a characteristic respiration rate. It will be understood that respiration rate and a characteristic respiration rate may be derived from any suitable signal obtained using a sensor capable of measuring the respiration of a patient, such as patient 40 (FIG. 2). For example, the respiration rate of a patient may be derived from a signal obtained from a flow meter or a chest band sensor. The signal may also be derived from other biological signals (i.e., biosignals) captured by one or more sensors of a suitable biosignal measurement system. For example, the signal may be derived from PPG signal data received from a pulse oximetry system such as pulse oximetry system 10 (FIG. 1), or from other biosignals including transthoracic impedance signals, capnograph signals, nasal thermistor signals, and/or electrocardiogram (EKG) signals. Although the techniques disclosed herein are described in terms of a respiration signal derived from a PPG signal, the disclosed techniques may be applied to any respiration signal or any other biosignals where cyclic phenomena are captured by the measurement system.

In some embodiments, a patient's respiration rate may be derived by obtaining a signal (e.g., PPG signal 450) from a sensor (e.g., oximeter 420) coupled to the patient, transforming the signal (e.g., using a continuous wavelet transform) to generate a primary scalogram from the wavelet transform as described above with respect to FIGS. 3(a) to 3(e), and analyzing a band of the primary scalogram (e.g., band B of FIG. 3(c)). For example, the scale or range of scales at which the band may appear on the primary scalogram is related to the frequency of the patient's breathing, or the patient's respiration rate.

In some embodiments, a patient's respiration rate may be determined by analyzing a ridge selected from the band of the primary scalogram (e.g., ridge B of band B in FIG. 3(c)). For instance, the primary scalogram may contain ridges corresponding to, among others, the pulse ridge in the pulse scale-range, e.g., corresponding to a characteristic frequency of 1 Hz, and the respiration ridge in the respiration scale-range, e.g., corresponding to a characteristic frequency of 0.3 Hz. In some embodiments, only the primary scalogram is used to identify or detect ridges. Optionally, in other embodiments, the primary scalogram may be used to compute one or more secondary scalograms after the pulse ridge loci are extracted. The secondary scalograms may be based on any suitable mapping of the primary scalogram (e.g., SWFD), that results in a secondary signal. These secondary scalograms may contain ridge components corresponding to the respiration scale-range. The primary and secondary scalograms can be computed using a predetermined time period within the signal and the primary scalogram (e.g., a five-second time period) or any other suitable time period. In some embodiments, a moving time period or window may be used to perform the scalogram computations. Once the primary, and in some embodiments, secondary scalograms, have been computed, ridges may be detected and identified (e.g., using processor 412) within these scalograms in the respiration scale-range. Such an identification or detection may be performed by selecting ridges that are within an acceptable breath frequency, e.g. 12-18 breaths per minute, or 0.2-0.3 Hz. Any suitable identification method may be used to select ridges within the respiration scale range. The technique described in this paragraph is described in more detail in U.S. patent application Ser. No. 12/245,326, filed Oct. 3, 2008, entitled "SYSTEMS AND METHODS FOR RIDGE SELECTION IN SCALOGRAMS OF SIGNALS," which is incorporated by reference herein in its entirety.

In some embodiments, a portion of the signal (e.g., PPG signal 450) may be used to obtain information about the patient's respiration rate. For example, a portion of the signal (e.g., an upstroke of signal 450) obtained from patient 40 (e.g., using oximeter 420) may be selected. The portion may be mirrored about a desired vertical axis to create a symmetrical pulse that includes the original signal portion and a new portion that mirrors the original selected portion. This technique may be repeated for another, different portion of the signal (e.g., a downstroke of signal 450) to create a second symmetrical pulse. The first and second pulses that have been created through the mirroring technique may be combined to create a new signal. The new signal may be transformed in any suitable manner, including for example, by using a wavelet transform. A scalogram may be generated based at least in part on the transformed signal as described with respect to FIGS. 3(a) and 3(b). From the scalogram, a time-scale band may be identified from which further information (e.g., ridge information or off-ridge information) may be extracted. Further transformation of the information may create a second transformed signal that may then be used to generate a second scalogram. From the second scalogram, a region may be analyzed (e.g., a ridge fragment may be selected by processor 412 and a sum along amplitudes technique may be applied to a portion of the band corresponding the selected ridge fragment to create a plot and identify a first peak or edge) to derive the patient's respiration rate. The technique described in this paragraph is described in more detail in U.S. Provisional Patent Application No. 61/077,062, filed Jun. 30, 2008, entitled "DERIVING PHYSIOLOGICAL PARAMETERS FROM PLETHYSMOGRAPH BY MIRRORING UPSTROKE OR DOWNSTROKE," which is incorporated by reference herein in its entirety.

In addition to respiration rate, the blood pressure and characteristic blood pressure of a patient also may be derived from any suitable signal (i.e., PPG signal 450) using, for example, system 10 or system 400. For example, blood pressure may be measured invasively using an arterial line or may be measured non-invasively using a sphygmomanometer. In some embodiments, blood pressure may be measured using any continuous non-invasive blood pressure ("CNIBP") approach, as more fully described in Chen et al. U.S. Pat. No. 6,599,251, entitled "CONTINUOUS NON-INVASIVE BLOOD PRESSURE MONITORING METHOD AND APPARATUS," which is incorporated by reference herein in its entirety. The technique described by Chen et al. may use two sensors (e.g., ultrasound or photoelectric pulse wave sensors) positioned at any two locations on a subject's body where pulse signals are readily detected. For example, sensors may be positioned on an earlobe and a finger, an earlobe and a toe, or a finger and a toe of a patient's body.

In some embodiments, an individual probe or sensor (i.e., sensor 12) may be used with a detector (i.e., detector 18) positioned anywhere suitable on patient 40 (i.e., in an area where a strong pulsatile flow may be detected, such as over arteries in the neck, wrist, thigh, ankle, ear, or any other suitable location) to detect a PPG signal for use with a CNIBP monitoring system or pulse oximeter. The PPG signal may then be analyzed (i.e., using processor 412) and used to compute a time difference between two or more points in the detected PPG signal. From this time difference, reliable and accurate blood pressure values may be computed on a continuous or periodic basis. In some embodiments, multiparameter patient monitor 26 may be configured to display an estimate of both of the patient's blood pressure and respiration rate as calculated by monitor 14.

In some embodiments, system 10 may include a calibration device that may be powered by monitor 14, a battery, or by a conventional power source such as a wall outlet, and that may include any suitable blood pressure calibration device. For example, the calibration device may take the form of any invasive or non-invasive blood pressure monitoring or measuring system used to generate blood pressure values used in calibrating CNIBP monitoring. Such calibration devices may include, for example, an aneroid or mercury sphygmomanometer and occluding cuff, a pressure sensor inserted directly into a suitable artery of a patient, an oscillometric device or any other device or mechanism used to sense, measure, determine, or derive blood pressure. In some embodiments, the calibration device may include a manual input device used by an operator to manually input blood pressure values obtained from some other source (i.e., an external invasive or non-invasive blood pressure measurement system). In some embodiments, processor 412 may be coupled to the calibration device.

In some embodiments, the calibration device may access blood pressure values stored in memory (e.g., RAM, ROM, or a storage device). For example, the calibration device may access blood pressure values from a relational database stored within the calibration device, monitor 14, or multi-parameter patient monitor 26. The blood pressure values generated or accessed by the calibration device may be updated in real-time, resulting in a continuous source of blood pressure values for use in continuous or periodic calibration. Alternatively, the blood pressure values generated or accessed by the calibration device may be updated periodically, and calibration may be performed on the same periodic cycle. In some embodiments, the calibration device may be connected to monitor 14. In other embodiments, the calibration device may be a stand-alone device that may be in wireless communication with monitor 14. The blood pressure values may then be wirelessly transmitted to monitor 14 for use in calibration. In still other embodiments, the calibration device may be completely integrated within monitor 14.

In some situations, one or more of a patient's physiological parameters may be distinctly altered if the patient is made aware that one or more of the physiological parameters is being observed or monitored by a clinician, and this alteration may undesirably result in a parameter value being reported or displayed that is not the characteristic value. For example, a clinician's interaction with the patient during observation of the respiration rate may cause the patient, or the probe being used in connection with monitoring the respiration rate, to move, which may deteriorate any suitable signal (e.g., a PPG signal) from which the respiration rate may be derived. Alternatively, the patient may breathe at a different rate or at an irregular rate when the clinician is present (e.g., because the patient may be speaking to the clinician, or because the patient may breathe faster or slower out of nervousness, self-consciousness, or anxiety). In some instances, the patient may breathe in a different cyclical pattern (e.g., the time periods of inhalation and exhalation may change, in relation to one another). In some instances, a clinician's interaction with the patient, the patient's perception of the clinical environment, and/or the patient's discomfort caused by the inflation of a blood pressure cuff on the patient, may increase the patient's anxiety and may undesirably increase the patient's blood pressure. The increase in blood pressure may diminish as the patient becomes more relaxed, for example as the blood pressure cuff deflates or as the patient becomes comfortable in the clinician's presence. It may therefore be clinically important to report a characteristic physiological parameter value that is not affected by or altered as a result of the patient's interaction with the clinician or the clinical environment. The characteristic physiological parameter value may provide a better indication of the patient's true status and/or may provide a better prediction of the patient's outcome (e.g., the characteristic respiration rate may be used with a patient scoring method, such as the CURB-65 score, a predictor of patient mortality associated with pneumonia).

Figure 6:
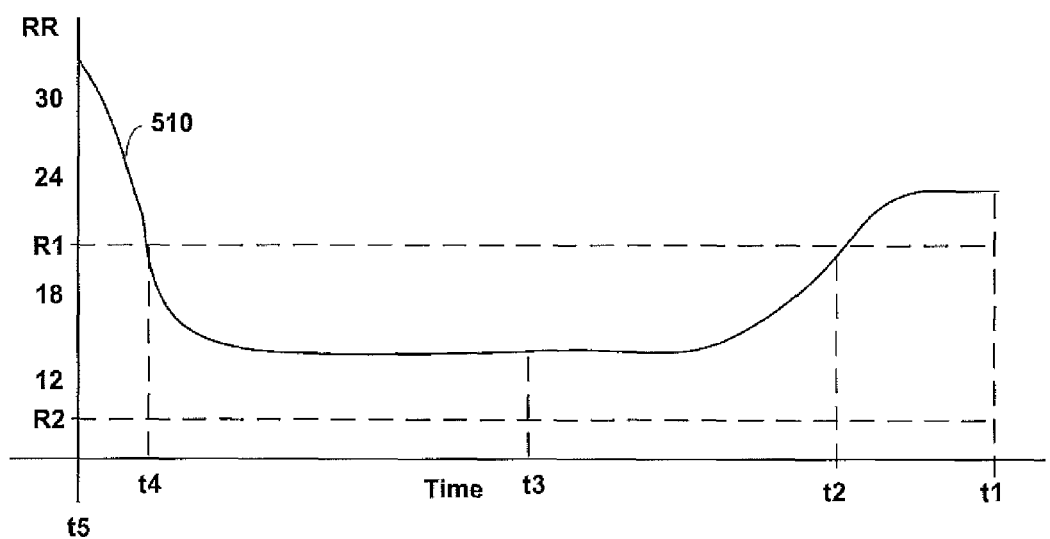
FIG. 6 shows a graphical illustration of a patient's respiration rate used in deriving a characteristic respiration rate in accordance with an embodiment.

The characteristic respiration rate may be derived from the respiration rate in any suitable manner. For example, the characteristic respiration rate may be obtained from analyzing the patient's respiration rate from any suitably defined time period occurring before a triggering event, such as the patient's interaction with the clinician. FIG. 6 shows a graphical illustration of a patient's respiration rate 510 used in deriving a characteristic respiration rate in accordance with an embodiment. Respiration rate 510 may be derived from any suitable signal (e.g., PPG signal 450) and/or may be graphically represented over any suitable time period t1 to t5, where t1 is closest in time to the present time. In some embodiments, the graphical illustration of respiration rate 510 may correspond to the characteristic frequencies of the breathing ridge, ridge B of band B in FIG. 3(c), over time. It will be understood that t1 may represent the present time, or some time separated from the present time by any suitable pre-set delay defined by processor 412 or microprocessor 48 (e.g., two minutes preceding a patient/clinician interaction at the present time). Time t1 may be defined as the time when a clinician chooses to obtain a patient's characteristic respiration rate (e.g., by selecting CRR option 530 from display 500 in FIG. 9), or time t1 may be a time that includes a pre-set delay prior to choosing to obtain a patient's characteristic respiration rate. In some embodiments, time period t1 to t5 may include two minutes, five minutes, or ten minutes. In some embodiments, respiration rate 510 may be derived by processor 412 or microprocessor 48 from the patient signal continuously or at a pre-set interval (e.g., every five or ten seconds) although respiration rate 510 may only be graphically represented over the discrete time period t1 to t5. Respiration rate 510 may vary over time period t1 to t5 and may increase at certain times due to any suitable event (e.g., a patient is aware that respiration rate 510 is being observed and/or monitored, patient 40 moves or oximeter 420 moves on the patient's body, the patient is speaking or has become nervous/anxious/self-conscious). It will be understood that the respiration rate values shown on the vertical axis of FIG. 6 are representative only and may include any suitable clinical range depending on the age and/or health of the patient.

In some embodiments, a characteristic respiration rate may be derived from the average value of respiration rate 510, the average value of respiration rate 510 with outlying respiration rate values removed (e.g., where outlying values are defined by processor 412 or microprocessor 48), a weighted average value of respiration rate 510 (e.g., where a weighting factor is defined by processor 412 or microprocessor 48 and may be related to a confidence measure), the median value of respiration rate 510, or the mode value of respiration rate 510, from time t5 to time t1. Alternatively, a characteristic respiration rate may be derived over a shorter time period. For example, if time period t1 to t5 encompasses five minutes or ten minutes, and time period t1 to t3 encompasses 2.5 minutes or five minutes, respectively, then two characteristic respiration rate values may be derived and/or displayed over time periods t5 to t3 and t3 to t1, respectively. Alternatively, any other suitable number of characteristic respiration rate values may be derived over time period t1 to t5.

In some embodiments, a characteristic respiration rate may be derived from respiration rate 510 values that do not exceed a pre-defined respiration rate threshold R1. For example, for a given patient 40, processor 412 or microprocessor 48 may define a threshold R1, where respiration rate values above threshold R1 may be associated with events (e.g., patient movement or probe movement, patient awareness of respiration rate 510 being monitored, or generally, patient anxiety or self-consciousness that may alter respiration rate 510) that may undesirably skew the derivation of a characteristic respiration rate and those values may not be used to derive the characteristic respiration rate. In FIG. 6, those respiration rate 510 values between times t2 and t4 may be used to derive a characteristic respiration rate. In some embodiments, processor 412 or microprocessor 48 may also define a lower respiration rate threshold R2, where values below such threshold R2 also may not be used to derive the characteristic respiration rate. Lower threshold R2 may be useful in preventing situations where a patient intentionally slows their respiration rate or respiration cycle (e.g., in response to observing a clinician or as a means of counteracting the effects of anxiety or self-consciousness) from being used to derive a characteristic respiration rate.

Figure 7:
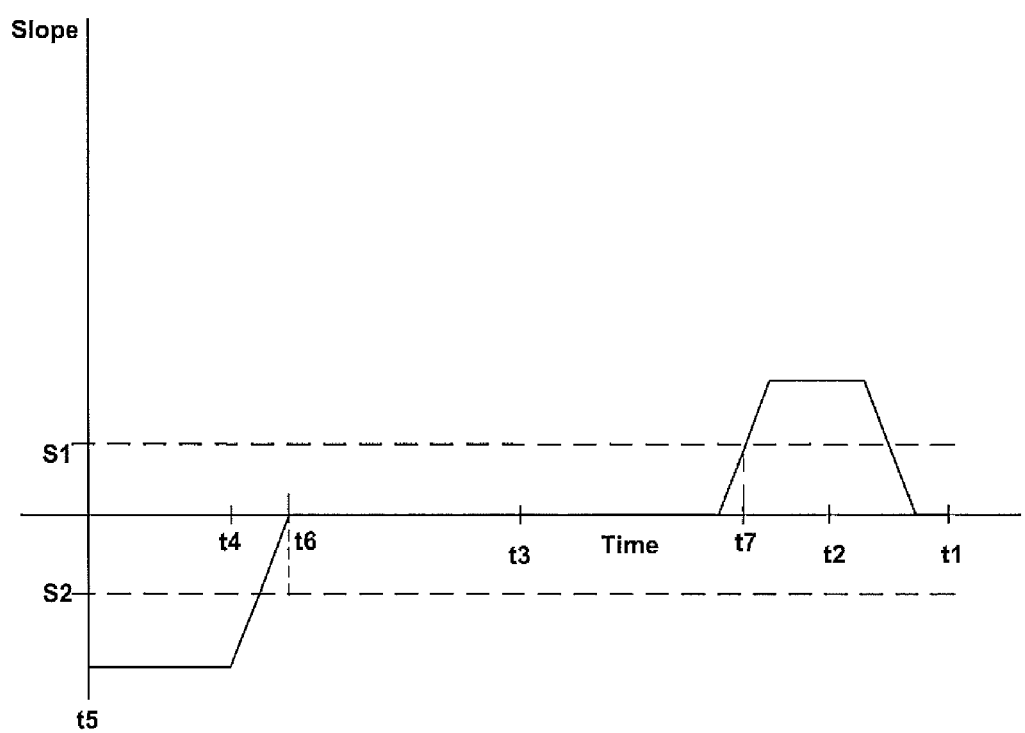
FIG. 7 shows a graphical illustration of the slope of the patient's respiration rate used in deriving a characteristic respiration rate in accordance with an embodiment.

In some embodiments, the slope of respiration rate 510 over any suitable time period may also be used to derive a characteristic respiration rate. FIG. 7 shows a graphical illustration of the slope 700 of the patient's respiration rate 510 used in deriving a characteristic respiration rate in accordance with an embodiment. Slope 700 may fall between upper slope threshold S1 and lower slope threshold S2, or may exceed one or both thresholds. Thresholds S1 and S2 may be pre-defined by processor 412 or microprocessor 48 with respect to a particular patient 40, and as with respiration rate thresholds R1 and R2, may be used to identify and exclude the effect on the derivation of a characteristic respiration rate of events that undesirably altered the patient's respiration rate 510. In some embodiments, slope thresholds S1 and S2 may provide a more accurate derivation of the characteristic respiration rate by providing a narrower time period t6 to t7 over which respiration rate 510 values may be used (e.g., narrower than time period t2 to t4 over which respiration rate 510 values may be used in FIG. 6), or a more sensitive measure of detecting and excluding undesirable respiration events.

Figure 8:
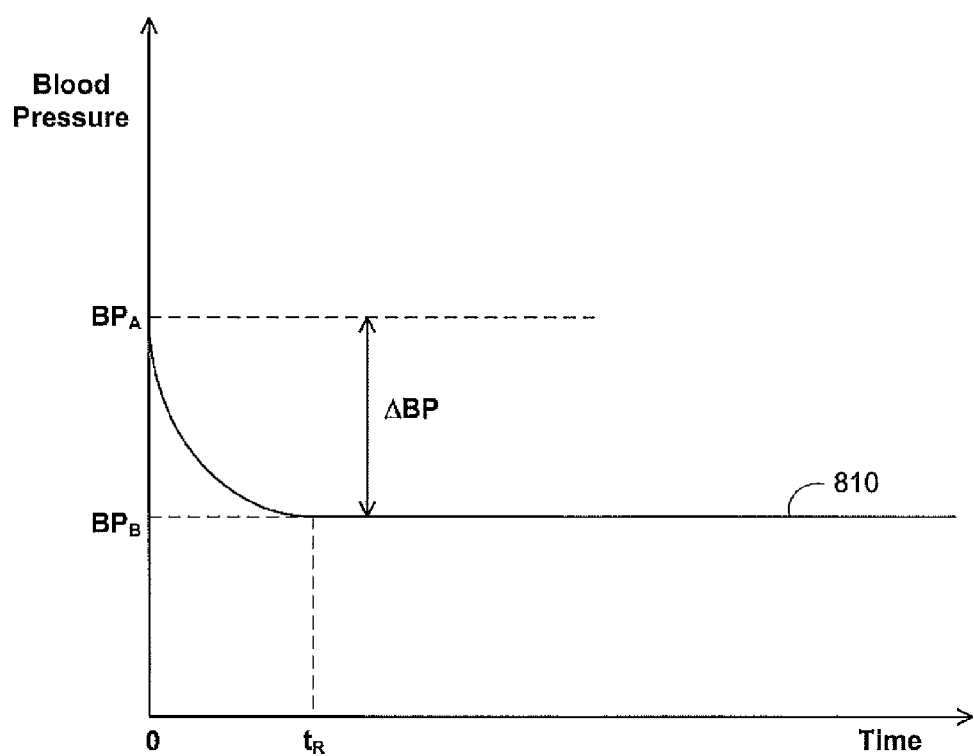
FIG. 8 shows a graphical illustration of a patient's blood pressure used in deriving a characteristic blood pressure in accordance with an embodiment.

The characteristic blood pressure may be derived from the patient's blood pressure in any suitable manner. For example, the characteristic blood pressure may be obtained by analyzing the patient's blood pressure following the most recent triggering event, such as the patient's interaction with the clinician. FIG. 8 shows a graphical illustration of a patient's blood pressure 810 used in deriving a characteristic blood pressure in accordance with an embodiment. The initial blood pressure reading on curve 810 may be taken using any suitable approach described above during or immediately following a triggering event. The triggering event may result in an increased, or in some instances, a decreased blood pressure value from the patient's baseline, or characteristic, blood pressure. In some embodiments, a triggering event may be detected by the patient's blood pressure ascending to or falling below a threshold value pre-defined by microprocessor 48 or processor 412. The initial blood pressure reading, $BP_A$, is shown in FIG. 8 at time zero. In some embodiments, this initial blood pressure reading may be made using the calibration device (e.g., a blood pressure cuff) such that at time zero, the CNIBP value for the patient is equivalent to initial blood pressure reading $BP_A$ obtained using the calibration device. Future blood pressure readings using the calibration device may be made to recalibrate the CNIBP system.

Figure 10:
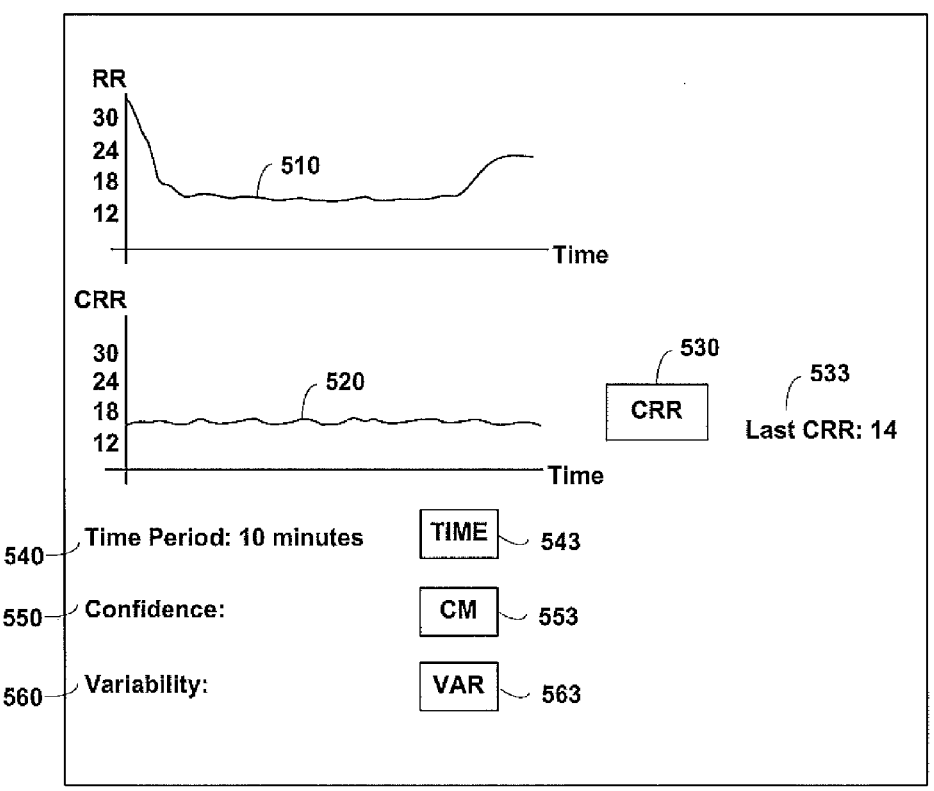
FIG. 10 shows an illustrative display for monitoring one or more of a patient's characteristic physiological parameters in accordance with an embodiment.

Following initial blood pressure reading $BP_A$, the patient's CNIBP may be tracked until the patient has fully relaxed following the last, or most recent, triggering event and the patient's blood pressure may reach a baseline, or characteristic, value $BP_B$ at or immediately preceding relaxation time $t_R$. These reduced blood pressure values may be asymptotic to a stable value, such as +/−4 mmHg, over a period of time longer than the respiratory rate. For example, $BP_B$ may reach a value of +/−4 mmHg over 10 seconds. Further, the patient's CNIBP reading may converge to a stable value of a period of time of approximately 5 to 10 minutes. $BP_B$ may be recorded as the characteristic blood pressure for the patient and may be displayed in any suitable manner, such as on display 500 (FIG. 10). The incremental increase between $BP_B$ and $BP_A$ may differ between different patients, as $BP_B$ may represent a characteristic blood pressure individualized to the patient, and therefore a constant offset blood pressure value may not be used to determine characteristic blood pressure $BP_B$ from initial blood pressure reading $BP_A$.

In some embodiments, relaxation time $t_R$ may be established initially using a mean value of times observed for blood pressure to reach a characteristic blood pressure value in a representative patient population. Alternatively, relaxation time $t_R$ may be taken as a particular threshold value of a parameterized CNIBP curve 810. For example, as the patient's CNIBP is tracked and recorded any suitable number of times following the triggering event at time zero, the slope between the recorded points of CNIBP curve 810 may be derived. Relaxation time $t_R$ may be taken as the time at which the slope of CNIBP curve 810 reaches a pre-determined desired threshold, such as where the slope equals zero or no longer has a negative value. In some embodiments, relaxation time $t_R$ may be interpolated using previous CNIBP curves and previous relaxation time $t_R$ values obtained from the particular patient, or may be derived from a running average of relaxation time $t_R$ values previously recorded for that patient. In some embodiments, various features of CNIBP curve 810 also may be analyzed (e.g., whether the slope of CNIBP curve 810 is still negative, or is still increasing or decreasing, at relaxation time $t_R$) to determine whether the reported characteristic blood pressure $BP_B$ is associated with a high or low confidence.

In some embodiments, CNIBP curve 810 also may be used to derive information about patient anxiety, which may be useful during a clinician exam or in situations where the patient's truthfulness is being assessed (e.g., during a lie detector test). For example, the difference $\Delta BP$ between the patient's initial blood pressure reading $BP_A$ and characteristic or baseline blood pressure $BP_B$ may be an indicator of patient stress by quantifying the change in the patient's blood pressure as a possible result of the triggering event. Also, relaxation time $t_R$, or the amount of time needed for the patient to reach a characteristic blood pressure $BP_B$, may be used as a relaxation index, as it may indicate the patient's ability to respond to, or recover from, anxiety-producing situations.

In some embodiments, the characteristic blood pressure and anxiety analysis described above may be used to assess a patient's blood pressure within a controlled repeatable stressful environment (e.g., during a cardiac stress test) using standard criteria. The characteristic blood pressure $BP_B$, relaxation time or relaxation index $t_R$, and stress indicator $\Delta BP$ may be used in conjunction with other stress measures or may be incorporated as part of a scoring system to clinically assess the patient.

In some embodiments, stress indicator $\Delta BP$ or relaxation time $t_R$ may be normalized to remove some statistical error before being used in patient assessment. For example, stress indicator $\Delta BP$ may be normalized by initial blood pressure $BP_A$, characteristic blood pressure $BP_B$, or a weighted mean of the two blood pressure readings. Relaxation time $t_R$ may be normalized by an average value of the relaxation time observed in a representative patient population. In addition, stress indicator $\Delta BP$ and relaxation time $t_R$, or normalized values of these measures, also may be combined in any suitable manner (e.g., added, multiplied, subtracted, or divided) to provide further information for assessing patient anxiety.

In some embodiments, one or more confidence measures may be used in association with characteristic physiological parameter values. For example, pre-defined static thresholds (e.g., as described above with respect to thresholds R1, R2, S1, and S2 in FIGS. 6-7) may function as confidence measures in that the thresholds may be used to exclude those respiration rate values that fall below or exceed the thresholds from being used in deriving the characteristic respiration rate. In some embodiments, only those blood pressure values on CNIBP curve 810 that fall within pre-defined high and low blood pressure thresholds (e.g., predefined by processor 412 or microprocessor 48) may be used to derive characteristic blood pressure $BP_B$ with a higher confidence. In addition, whether the slope of the patient's CNIBP curve 810 at relaxation time $t_R$ has a negative value, a zero value, or a rapidly increasing or decreasing value, may be used to determine whether the reported characteristic blood pressure $BP_B$ is associated with a high or low confidence.

Alternatively, the characteristic respiration rate may be derived dynamically using a weighted average of respiration rate 510 values over a defined time period (e.g., over a five or ten minute window preceding the clinician/patient interaction or preceding the interaction by a pre-defined delay), where one or more confidence measure(s) may represent the weighting factor(s) applied to the derived respiration rate 510 values. In some embodiments, the characteristic respiration rate may be derived using the following equation:

$$CRR_{tp}=(aRR_{t4}+bRR_{t3}+cRR_{t2}+dRR_{t1}+eRR_{tp})/(a+b+c+d+e) \quad (18)$$

where "CRR" is the characteristic respiration rate to be reported, t1 through t4 are points in time substantially similar to points t1 through t4 described with respect to FIG. 6. and may be characteristic of the respiration rate over any suitable time period that may or may not include a pre-defined delay (e.g., characteristic of the respiration rate up to a time preceding the present by two minutes). The variable "RR" is the respiration rate value obtained from the respiration signal (PPG signal 450) using any of the methods described above at a given point in time, where the particular time is indicated by the subscript notation. In some embodiments, the points in time may be pre-defined (e.g., respiration rate values may be determined from the respiration signal every ten or fifteen seconds). It will be understood that equation (18) is illustrative and that the characteristic respiration rate may be determined using any suitable number of respiration rate values obtained over any suitable time period.

The confidence measure factors a, b, c, d, and e associated with each time-based "RR" value may be a function of the respiration signal (e.g., PPG signal 450) in that the factors may be derived from the signal (e.g., each factor may be related to a historical amplitude value of the breathing band B in FIG. 3(c) determined at a given point in time). The confidence measure factors may act as weighting factors in determining the overall characteristic respiration rate and each factor may have a dynamic value that changes as the respiration signal changes with time. In some embodiments, a particular time-based respiration rate value may fall below or may exceed a pre-defined threshold (e.g., due to the patient experiencing a respiration event) as defined by processor 412 or microprocessor 48. The value of the confidence measure derived using that respiration rate value may be impacted such that multiplying the confidence measure by the respiration rate value may result in that respiration rate value being excluded from deriving the characteristic respiration rate (e.g., by dropping out of equation (18)). In some embodiments, only those respiration rate values falling within pre-defined thresholds may be used to derive confidence measures and thereafter used in equation (18) to derive a characteristic respiration rate. In some embodiments, the characteristic respiration rate may be reported and/or displayed (e.g., on display 500 of FIG. 10) along with the confidence measure(s) to provide the clinician with information regarding the quality of the estimation of the characteristic respiration rate. The confidence measure may also be used to modify factor a, which may then be multiplied by the current determined respiration rate and added to the previous value of respiration rate weighted a by factor of (1−a),) (i.e. in the form of an Infinite Impulse Response filter). A slower response may be obtained by using a fraction of a to weight the current determined respiration rate.

In some embodiments, any suitable features of a scalogram (e.g., the scalogram of FIG. 3(c)) may be used to derive the confidence measure(s) described above with respect to characteristic respiration rate. For example, the ridge length of a band of interest (e.g., band B) identified from a scalogram of the PPG signal, modulation of the scalogram at the band of interest and/or the energy of the scalogram as determined by a sum along amplitudes technique may be used to derive one or more confidence measures. In some embodiments, any suitable averaging of these scalogram features, such as a weighted average, or any linear regression models created with the features may be used to derive the confidence measure(s). In addition, the length of the signal segment used to determine respiratory rate relative to the total length of the signal segment under investigation may also be used to derive the confidence measure(s). The total number of breaths counted for respiration rate may also be used to derive the confidence measure(s). In an embodiment, the area under the sum along amplitudes plot in the vicinity of the selected respiration rate relative to the total area under the sum along amplitudes plot may be used to derive the confidence measure(s). The number of peaks in the sum along amplitudes plot may also be used to derive the confidence measures. For example, a single peak in the sum along amplitudes plot may be indicative of a higher confidence as compared to more than one peak.

Figure 9:
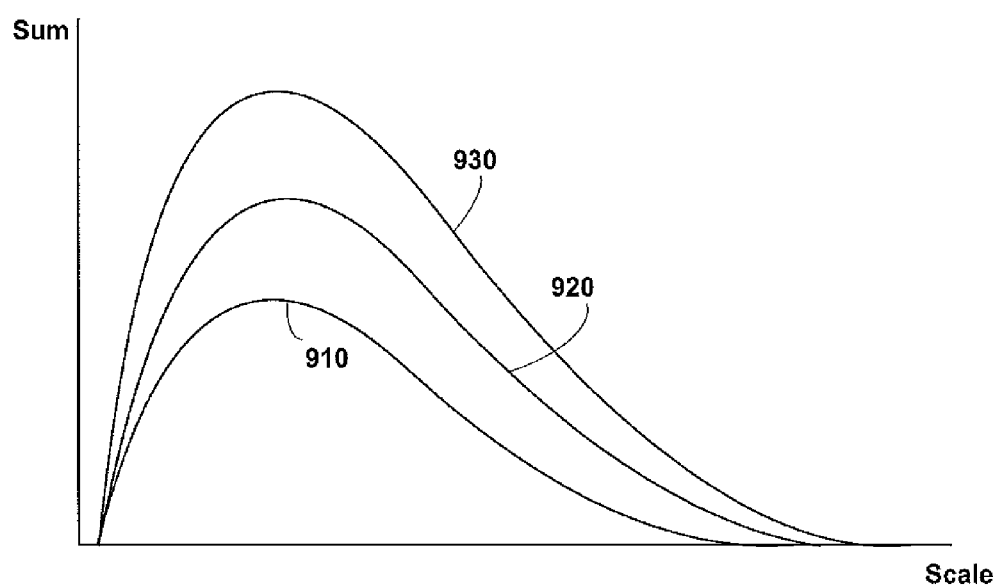
FIG. 9 shows a graphical illustration of a sum along amplitudes for a region of a scalogram in accordance with an embodiment.

In some embodiments, a sum along amplitudes technique may be used to derive one or more respiration rate confidence measures, by locating portions of the respiration signal that may be associated with respiration events and excluding those portions from being used to derive a confidence measure and/or a characteristic respiration rate. FIG. 9 shows a graphical illustration of a sum along amplitudes for a region of a scalogram (e.g., the scalogram in FIG. 3(b)) in accordance with an embodiment. A sum along amplitudes technique may be applied to at least a portion of the band (e.g., band B) corresponding to the selected ridge from the scalogram or, in some embodiments, at least a portion (e.g., the identified stable region) of a selected secondary scalogram derived at least in part using the first scalogram using any suitable method. The technique of applying a sum along amplitudes may be applied to any secondary wavelet feature decoupling method of any suitable original signal (e.g., signal 450). The sum along amplitudes technique also may be applied to any continuous wavelet transform of any suitable signal, such as a wavelet transform of the original PPG signal 450. The sum along amplitudes technique may sum the amplitudes (e.g., the energy) for each scale within a range of scales (e.g., a range of scales corresponding to the location of the breathing band) across a time window (e.g., any suitable time window used to derive a characteristic respiration rate, such as thirty seconds, or a minute, or two minutes or five minutes). The resulting sum(s) may be plotted as a function of any suitable value, such as scale value, as shown in FIG. 9. The resulting area underneath each plotted curve in FIG. 9 may then correspond to the energy associated with the portion of the band corresponding to the selected ridge from the scalogram. Processor 412 or microprocessor 48 may analyze the sums to determine whether certain values of the patient's respiration rate 510 may be used in deriving characteristic respiration rate.

In FIG. 9, three curves 910, 920, and 930 are shown. Each curve may be generated within the same range of scales using a scalogram at different time windows or each may be generated within the same range of scales using different scalograms. The area under curve 910 (e.g., the energy of the scalogram within the range of scales for a given time window) may be less than the area under curve 920 (e.g., the energy of the scalogram within the range of scales for a second time window), which may be less than the area, or energy, under curve 930 (e.g., the energy of the scalogram within the range of scales for a third time window). If the range of scales used to generate curves 910, 920, and 930 correspond to the characteristic frequency or frequencies at which information about a patient's respiration rate 510 may be contained in the original patient signal (e.g., PPG signal 450), then an increase in area underneath curves 920 and/or 930 in FIG. 9 may indicate an increase in energy of the patient signal due to increased breathing effort. Increased breathing effort may be associated with a respiration event (e.g., the patient may be speaking to the clinician, or the patient may be breathing faster or slower out of nervousness, self-consciousness, or anxiety) that may not be characteristic of the patient's respiration rate. Processor 412 or microprocessor 48 may analyze the sums, as shown plotted in FIG. 9, to identify respiration events and exclude the respiration signal information and time window related to those respiration events from being used to derive a confidence measure and/or a characteristic respiration rate.

A patient's physiological parameters and characteristic physiological parameters may be presented or displayed to a clinician or a user of system 10 in any suitable manner. FIG. 10 shows an illustrative display for monitoring a patient's characteristic physiological parameters in accordance with an embodiment. In some embodiments, display 500 may be the same as, and may include some or all of the features of, display 28, and may be part of multi-parameter patient monitor 26. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's respiration rate and blood pressure and/or characteristic values of those parameters, as generated by monitor 14, on display 500.

Display 500 may be a cathode ray tube type, a flat panel display (as shown) such as a liquid crystal display (LCD) or a plasma display, or any other type of display now known or later developed. By way of example, display 500 may include a graphical representation of respiration rate 510 as a function of time, as derived from a signal (e.g., as derived by processor 412 or microprocessor 48 from a PPG signal obtained from patient 40 using sensor 12) using any suitable method described above. Any suitable time period 540 (e.g., the preceding ten minutes from the present time, or ten minutes preceding any suitably defined delay from the present time) may be used over which to display respiration rate 510. Respiration rate 510 may be presented graphically over time to aid a clinician or user of display 500 in observing the trending of respiration rate 510. Time period 540 may be displayed on display 500 and may be altered by a user selecting time option 543 (e.g., touching display 500 over time option 543). In some embodiments, time option 543 (and options 530, 553, and 563) may be depressible buttons that may be located on multi-parameter patient monitor 26, monitor 14, or on any other suitable device. In some embodiments, respiration rate 510 may be derived continuously or at a pre-set interval (e.g., every five or ten seconds), although respiration rate 510 may not be graphically represented on display 500. In such situations, a number (e.g., 12 breaths per minute) may be shown instead on display 500, representing the last respiration rate determination, or a user of display 500 may select an option (not shown) on display 500 to display the respiration rate either graphically or as an individual number. In some embodiments, any other suitable information may be provided on display 500 with respect to respiration rate 510, such as the average respiration rate, the median respiration rate, the mode respiration rate, or a weighted average respiration rate over time period 540, where such information may or may not be the same as the characteristic respiration rate.

Display 500 also may include a graphical representation of characteristic respiration rate 520 as a function of time, as derived from the respiration rate 510. In some embodiments, the time period over which respiration rate 510 may be displayed may not be the same time period over which characteristic respiration rate 520 may be displayed, as respiration rate 510 may be derived continuously or at a frequent and regular interval, whereas characteristic respiration rate 520 may be derived intermittently, over a variety of time periods, or only at the request of a user of display 500. It may still be important to represent characteristic respiration rate 520 graphically, however, to aid a clinician or user of display 500 in observing the trending of respiration rate 520. In some embodiments, characteristic respiration rate 520 may be graphically represented on display 500 and may be shown also as a number (e.g., 14 breaths per minute) representing the last characteristic respiration rate determination 533, or in some embodiments, only the last characteristic respiration rate determination 533 may be displayed. In some embodiments, particularly where the characteristic respiration rate 520 is only calculated at the request of a user of display 500, CRR option 530 may be included on display 500 and may be selected by a user of display 500 to derive a new characteristic respiration rate 520 using respiration rate 510 in any suitable manner.

In some embodiments, display 500 also may present any other suitable metrics and options related to characteristic respiration rate 520, including but not limited to, one or more confidence measure(s) 550 and related CM option 553, and variability 560 (e.g., the variance or the standard deviation of the characteristic respiration rate) and related VAR option 563. Confidence measure 550 may be displayed (and CM option 553 selected) to provide the user of display 500 with information regarding the quality of the characteristic respiration rate 520 This information may include a percentage to indicate the confidence measure 550, such as 95%. Further, this information may include an estimated standard deviation of the measured breaths per minute as compared to an average number of breaths per minute, such as 1, 2, or 3 standard deviations. Variability 560 may be displayed (and VAR option 563 selected) to indicate whether characteristic respiration rate 520 is representative of the patient's respiration rate 510. CM option 553 and/or VAR option 563 may be selected to remove confidence measure 550 and/or variability 560 from display 500 or alternatively to review historical values of confidence measure 550 and/or variability 560 over any suitable time period or suitable number of characteristic respiration rate 520 determinations. In an embodiment, characteristic respiration rate 520 may be presented together with a timestamp of the time at which the reported characteristic respiration rate 520 occurred. It will be understood that display 500 or multiparameter patient monitor 26 may be configured to display any other suitable information related to one or more patient physiological parameters and their characteristic values, including but not limited to, CNIBP curve 810, a confidence associated with characteristic blood pressure $BP_B$, and graphical, numerical, or historical representations of initial blood pressure $BP_A$, characteristic blood pressure $BP_B$, relaxation time or relaxation index $t_R$, and patient stress indicator $\Delta BP$.

Figure 11:
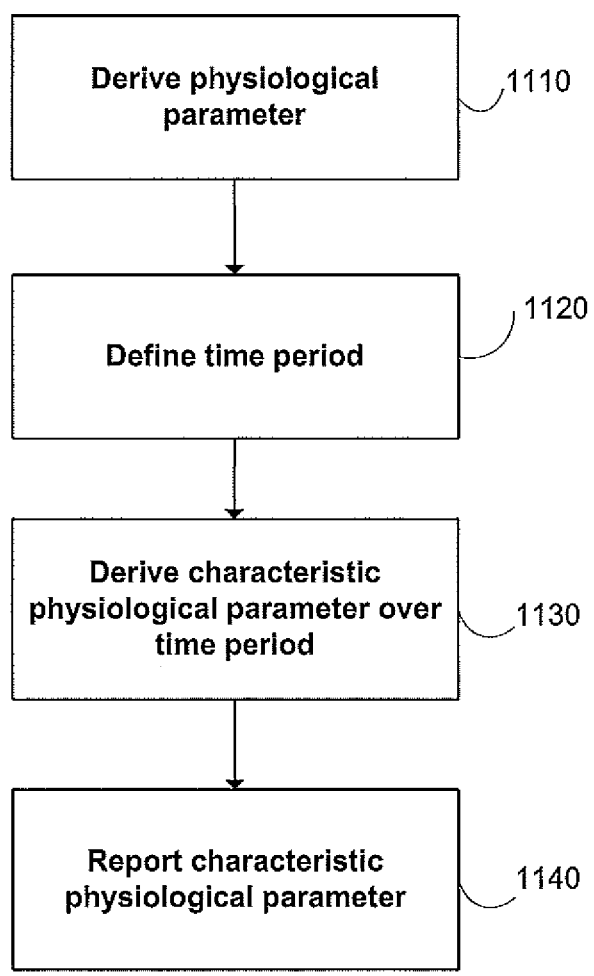
FIG. 11 is a flow chart of an illustrative process for deriving a characteristic physiological parameter in accordance with an embodiment.

FIG. 11 is a flow chart of an illustrative process 1100 for deriving a characteristic physiological parameter in accordance with an embodiment. Process 1100 may begin at step 1110, where a patient's physiological parameter may be derived using any suitable method. For example, respiration rate 510 may be derived by obtaining a signal (e.g., PPG signal 450) from a sensor (e.g., oximeter 420) coupled to the patient, transforming the signal (e.g., using a continuous wavelet transform) to generate a primary scalogram from the wavelet transform as described above with respect to FIGS. 3(a) to 3(e), and analyzing a band of the primary scalogram (e.g., band B of FIG. 3(c)). The scale or range of scales at which the band may appear on the primary scalogram may be related to the frequency of the patient's breathing, or the patient's respiration rate. As a further example, CNIBP curve 810 may be derived using an initial blood pressure cuff reading and subsequent CNIBP tracking of the patient's blood pressure using PPG signal 450.

In an embodiment, process 1100 may advance to step 1120, where any suitable time period is defined over which the patient's physiological parameter values may be used to derive a characteristic physiological parameter value. For example, the time period preceding a triggering event, such as a clinician/patient interaction (e.g., the previous two minutes, five minutes, or ten minutes), or any suitably defined time period separated from the triggering event by a defined delay may be used to derive the characteristic respiration rate. The time period following the last or most recent triggering event, up to and including at least relaxation time $t_R$, may be used to derive the characteristic blood pressure.

In an embodiment, process 1100 may advance to step 1130, where the patient's characteristic physiological parameter (e.g., characteristic respiration rate 520) may be derived using the time period defined in step 1120 using any suitable method. The patient's physiological parameter may be derived by processor 412 or microprocessor 48 (and in some embodiments, displayed on display 500) on a continuous basis or at a pre-set interval (e.g., every five or ten seconds). In an embodiment, the characteristic respiration rate may be derived as described above with respect to FIGS. 6-7, and the characteristic blood pressure may be derived as described above with respect to FIG. 8. In some embodiments, one or more confidence measures also may be associated with or used to derive the characteristic physiological parameter value. In an embodiment, a sum along amplitudes technique may be used to derive one or more confidence measures for the characteristic respiration rate.

In some embodiments, process 1100 may advance to step 1140, where the characteristic physiological parameter derived in step 1130 may be reported in any suitable manner. For example, the characteristic respiration rate and/or the characteristic blood pressure may be displayed on display 500. In some embodiments, the characteristic physiological parameter may be graphically represented and may be shown also as a number representing the last characteristic physiological parameter value reported, or in some embodiments, only the last characteristic physiological parameter value derived may be displayed (either automatically or in response to a user request). In some embodiments, particularly where the characteristic physiological parameter is only calculated at a user's request, a selectable option may be included to permit a user (e.g., a user of display 500) to derive a new characteristic physiological parameter value using the physiological parameter derived in step 1110 in any suitable manner. In some embodiments, any other suitable options (e.g., the variability of the characteristic respiration rate being reported, stress indicator, or relaxation index) may be reported.

Figure 12:
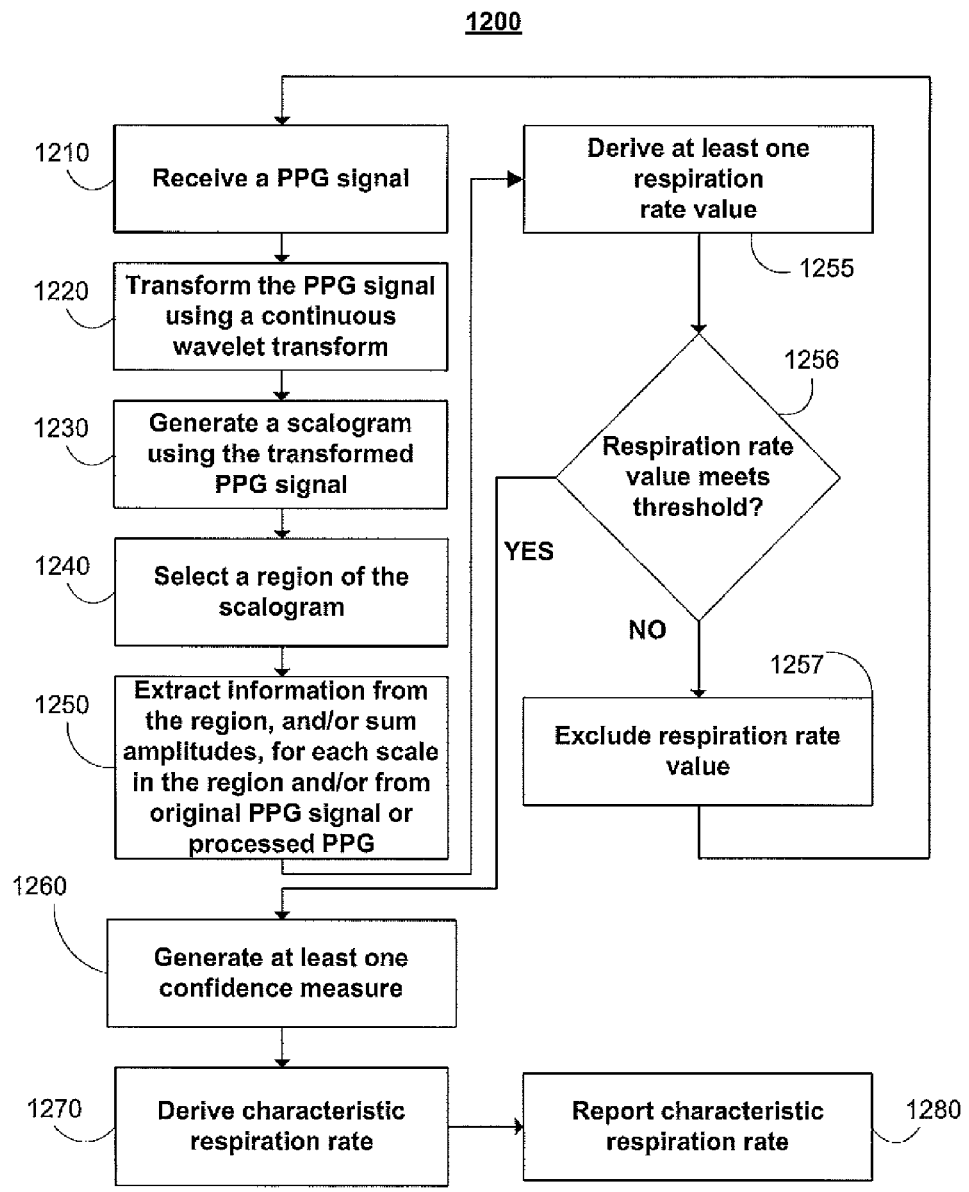
FIG. 12 is a flow chart of an illustrative process for deriving a characteristic respiration rate in accordance with an embodiment.

FIG. 12 is a flow chart of an illustrative process for deriving a characteristic respiration rate in accordance with an embodiment. Process 1200 may begin at step 1210, in which a PPG signal is received from a patient (e.g., sensor 12) using any suitable approach (e.g., signal 450 obtained using oximeter 420 in system 400 or sensor 12 in system 10). The PPG signal may be received continuously or at pre-set intervals by any suitable device, such as monitor 14 or multi-parameter patient monitor 26.

Process 1200 may advance to step 1220 upon receiving the PPG signal at step 1210. At step 1220, the PPG signal that was received at step 1210 may be transformed by processor 412 or microprocessor 48. For example, the PPG signal may be transformed using a continuous wavelet transform as described above using equation (9). Process 1200 may advance to step 1230 upon performing this transformation. At step 1230, a scalogram may be generated in any suitable manner and based at least in part on the transformed signal from step 1220. For example, the scalogram may be generated using the energy density function equation (10) and may include some or all of the features described above with respect to FIGS. 3(a), 3(b), and 3(c). In an embodiment, the scalogram of the PPG signal may include any suitable number of bands containing pulse information and respiration information, and each band may include a ridge. The ridge may be continuous or may include any suitable number of ridge fragments.

Process 1200 may advance to step 1240, where any suitable region of the scalogram may be selected. For example, a portion of the scalogram containing a ridge fragment may be selected. Alternatively, the entire scalogram may be selected. Process 1200 may advance to step 1250, where information about a ridge fragment may be extracted from the selected scalogram portion. Alternatively or additionally at step 1250, for each scale within the selected region of the scalogram, a sum of the amplitudes (e.g., the energy) across time at that scale may be obtained. Thus, for a region of the scalogram that may contain information about the patient's breathing (e.g., band B in FIG. 3(c)), any suitable number of sums may be calculated within a given time window. The technique may be applied by processor 412 or microprocessor 48 to at least a portion of the band corresponding to the selected ridge or at least a portion of the original scalogram. In an embodiment, processor 412 or microprocessor 48 may include any suitable software, firmware, and/or hardware, and/or combinations thereof for generating a sum along amplitudes vector and applying it to the selected region. In an embodiment, if more than one scalogram was generated at step 1230 (e.g., two scalograms may be generated from transforming two PPG signals received at step 1210), then the sum along amplitudes technique may be applied to a scalogram composite, or a superposition formed from the scalograms.

Process 1200 may then advance to step 1255. At step 1255, at least one respiration rate value may be derived from the PPG signal (e.g., by processor 412 or microprocessor 48) continuously or at a pre-set interval using any suitable approach as described above. Following step 1255, process 1200 may advance to step 1256, in which the respiration rate value may be analyzed (e.g., using processor 412 or microprocessor 48) to determine whether the respiration rate value meets any suitable threshold (e.g., does not fall below or exceed any of those thresholds described above with respect to FIGS. 6-7). If the respiration rate value meets the threshold, process 1200 may advance to step 1260 and select the respiration rate value to derive a characteristic respiration rate. If the respiration rate value does not meet the threshold, process 1200 may advance to step 1257 and exclude the respiration rate value from being used to derive the characteristic respiration rate. After step 1257, process 1200 may return to step 1210 in which a new PPG signal may be received to derive the respiration rate.

At step 1260, the respiration rate selected at step 1256 may be used to generate at least one confidence measure for a given point in time. In an embodiment, the amplitude, frequency, consistency in amplitude and/or frequency, or the length of a ridge in the selected scalogram may be used to generate at least one confidence measure. The confidence measure may be derived for a point in time that also may be the point in time for which the respiration rate value was derived at step 1255. In other words, for each point in time for which a respiration rate value is derived at step 1255 and meets the threshold at step 1256, a corresponding confidence measure may be derived at step 1260. In some embodiments, any suitable averaging of the scalogram features obtained from step 1250, such as a weighted average, or any linear regression models created with the features, may be used to derive the confidence measure(s). In some embodiments, a confidence measure may be derived for each point in time from the region of the scalogram selected in steps 1240 and 1256.

In some embodiments, process 1200 may advance to step 1270, where the at least one confidence measure generated in step 1260 and the respiration rate value derived at step 1255 and selected at step 1256 may be used to derive a characteristic respiration rate. In some embodiments, the use of the confidence measure with its related respiration rate value may cause that respiration rate value to be excluded (e.g., the weighted respiration rate value may fall below or exceed a threshold pre-defined by processor 412 or microprocessor 48) from deriving the characteristic respiration rate, as described above with respect to equation (18). In some embodiments, process 1200 may advance to step 1280 and may report the characteristic respiration rate in any suitable manner (e.g., as shown on display 500 of FIG. 10). In some embodiments, the characteristic respiration rate may not be reported unless requested by a user of display 500 or system 10/400. In some embodiments, process 1200 may advance automatically to step 1270 and the derivation of the characteristic respiration rate, whereas in some embodiments, step 1270 may not be undertaken until a particular request (e.g., a selection of CRR option 530 from display 500) is made.

Figure 13:
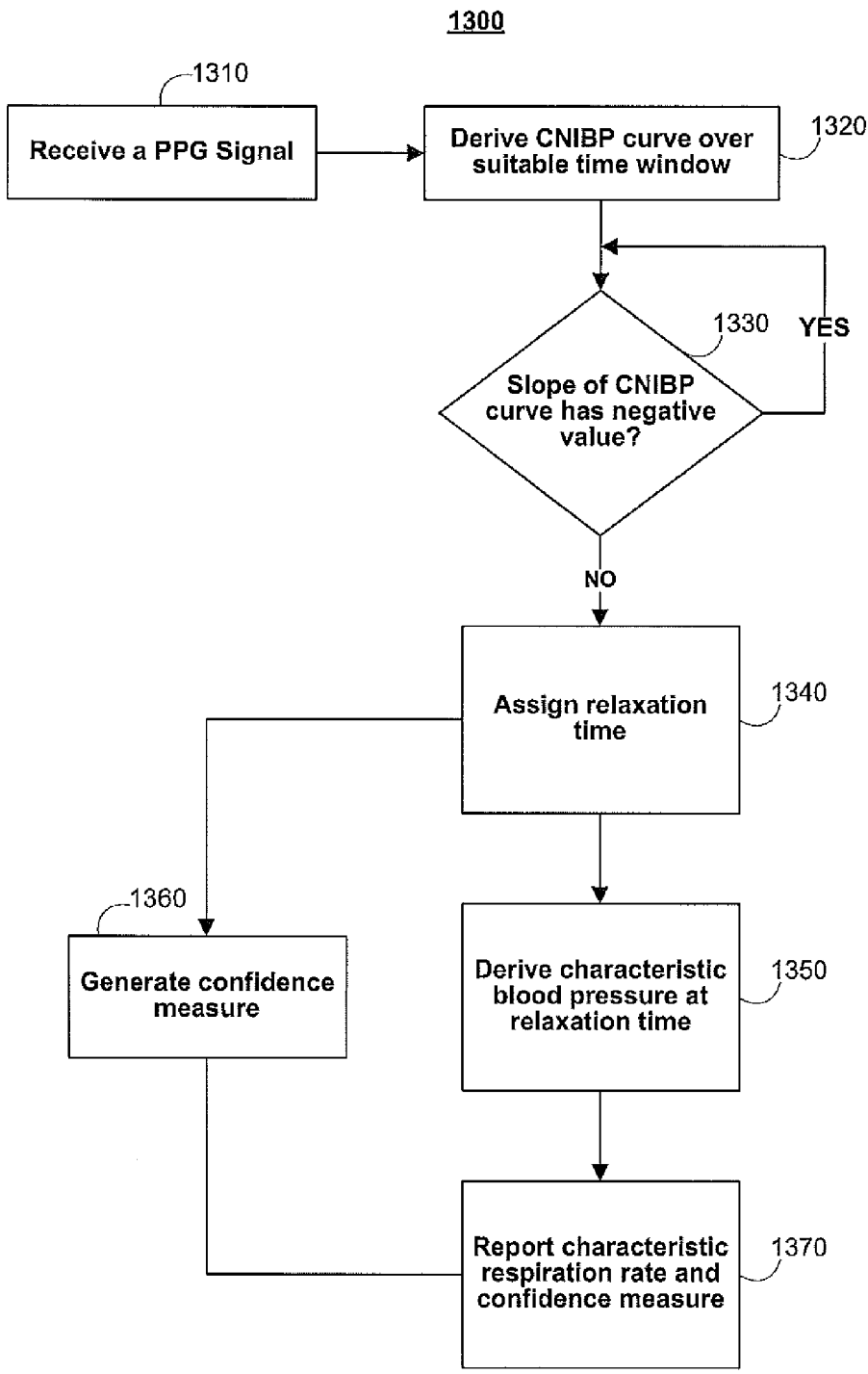
FIG. 13 is a flow chart of an illustrative process for deriving a characteristic blood pressure in accordance with an embodiment.

FIG. 13 is a flow chart of an illustrative process for deriving a characteristic blood pressure in accordance with an embodiment. Process 1300 may begin at step 1310, in which a PPG signal is received from a patient during and following a triggering event using any suitable approach (e.g., signal 450 is obtained during a patient/clinician interaction using sensor 12 in system 10). The PPG signal may be received continuously or at pre-set intervals by any suitable device, such as monitor 14 or multi-parameter patient monitor 26.

In some embodiments, process 1300 may advance to step 1320, where a CNIBP curve (e.g., CNIBP curve 810) may be derived from the PPG signal using any suitable approach as described above (e.g., using processor 412 or microprocessor 48). For example, an initial blood pressure value $BP_A$ may be obtained during the triggering event. System 10/400 may be used to derive the CNIBP curve after first using a calibration device, such as a blood pressure cuff, to calibrate system 10/400 to obtaining the patient's blood pressure. The CNIBP curve may be derived over any suitable time window, such as a period of time starting at a triggering event (e.g., a patient/clinician interaction) and continuing at least until a relaxation time $t_R$ has been reached or has passed. In some embodiments, certain thresholds pre-defined by processor 412 or microprocessor 48 may be used to prevent those CNIBP values that exceed or fall below the thresholds from being used in the CNIBP curve.

In some embodiments, process 1300 may advance to step 1330, in which the slope of the CNIBP curve may be analyzed by processor 412 or microprocessor 48 to determine whether, for example, the slope still has a negative value, or whether the slope is zero. If the slope of the CNIBP curve is still negative, then process 1300 may return to step 1330, as the relaxation time may not have occurred and the patient's blood pressure may not have reached a baseline, or characteristic, value following the triggering event. If the slope of the CNIBP curve is no longer negative (e.g., has a zero value), then process 1300 may advance to step 1340, at which the relaxation time may be assigned to the time at which the CNIBP curve first has a slope of zero after the triggering event. In some embodiments, if the patient's blood pressure has not been assessed before or no CNIBP curves related to the particular patient have been stored, then process 1300 may instead use a population mean value for the relaxation time and may derive the patient's characteristic blood pressure using the mean value.

It will be understood that, in some embodiments, the triggering event may cause a decrease in the patient's blood pressure, and it may be desirable to determine the characteristic blood pressure once the patient's blood pressure has resumed a characteristic value following the triggering event. For example, if a patient experiences a temporary drop in blood pressure (e.g., due to a medication, a physical or emotional condition, or any other suitable situation), then process 1300 may determine at step 1330 whether the CNIBP curve is no longer positive, or is no longer increasing from the dropped value as a result of the triggering event.

In some embodiments, process 1300 may advance to steps 1350 and 1360 simultaneously. At step 1350, a characteristic blood pressure $BP_B$ value may be derived from the CNIBP curve at the relaxation time. At step 1360, a confidence measure may be generated that may be associated with the characteristic blood pressure $BP_B$. In some embodiments, the slope value of the CNIBP curve at the relaxation time may be used by processor 412 or microprocessor 48 to associate the characteristic blood pressure $BP_B$ with a high or low confidence. For example, if the population mean value of the relaxation time is the time at which the characteristic blood pressure $BP_B$ is determined, but the slope of the patient's particular CNIBP curve is still negative at the mean relaxation time, then the characteristic blood pressure $BP_B$ from step 1350 may be associated with a low confidence, as the patient's blood pressure may not have returned to its baseline.

In some embodiments, process 1300 may advance to step 1370 and may report the characteristic blood pressure $BP_B$ and, in some instances, the associated confidence, in any suitable manner (e.g., on display 500). In some embodiments, the characteristic blood pressure $BP_B$ may not be reported unless requested by a user of display 500 or system 10/400. In some embodiments, process 1300 may advance automatically to steps 1330-1370 and the derivation of the characteristic blood pressure $BP_B$, whereas in some embodiments, steps 1330-1370 may not be undertaken until a particular request is made.

In some embodiments, process 1300 also may determine a stress indicator ΔBP from the difference between the patient's initial and characteristic blood pressure values determined at steps 1320 and 1350. Process 1300 may report ΔBP on display 500, along with relaxation time $t_R$, to provide information about the patient's anxiety level and the patient's ability to respond to anxiety-inducing situations.

It will be understood that the foregoing is only illustrative of the principles of the disclosure, and that the disclosure can be practiced by other than the described embodiments, which are presented for purposes of illustration and not of limitation.

What is claimed is:

1. A method for determining a characteristic respiration rate of a patient by a pulse oximeter, the method comprising:
   receiving, using the pulse oximeter, a photoplethysmographic (PPG) signal derived from a pulse oximetry sensor, wherein the pulse oximetry sensor is configured to detect light attenuated by the patient;
   determining, using the pulse oximeter, respiration rate values of the patient over time based at least in part on the PPG signal;
   detecting, using the pulse oximeter, a first respiration rate event, wherein the first respiration rate event is detected based at least in part on a first deviation in the respiration rate values;
   determining, using the pulse oximeter, a first altered portion of the respiration rate values based on the first respiration rate event;
   determining, using the pulse oximeter, the characteristic respiration rate of the patient based at least in part on a selected portion of the respiration rate values, wherein:
      the selected portion of the respiration rate values excludes the first altered portion of the respiration rate values;
      the selected portion of the respiration rate values occurs earlier in time than the first altered portion of the respiration rate values;
      the determining of the characteristic respiration rate is not based on the first altered portion of the respiration rate values; and
      the characteristic respiration rate is determined to assess a clinical status of the patient; and
   displaying, using an output of the pulse oximeter, the characteristic respiration rate.

2. The method of claim 1 further comprising:
   determining, using the pulse oximeter, blood pressure values over time based at least in part on the PPG signal, wherein:
      a first blood pressure value is determined based at least in part on a first blood pressure event; and
      the first blood pressure event is detected based at least in part on a deviation in the blood pressure values;
   identifying, using the pulse oximeter, a relaxation time based at least in part on the blood pressure values, wherein the relaxation time occurs later in time than the first blood pressure event; and
   deriving, using the pulse oximeter, a characteristic blood pressure of the patient based at least in part on a blood pressure value at the relaxation time, wherein the characteristic blood pressure is continuously derived to assess the clinical status of the patient.

3. The method of claim 2, further comprising analyzing, using the pulse oximeter, at least one of the first blood pressure value, the characteristic blood pressure, and the relaxation time to assess the anxiety of the patient.

4. The method of claim 1, wherein the first respiration rate event is detected based at least in part on the first altered portion of the respiration rate values reaching a threshold value.

5. The method of claim 1 wherein the first respiration rate event is detected based at least in part on the slope of the respiration rate values reaching a threshold value.

6. The method of claim 1 wherein the characteristic respiration rate is determined based at least in part on an average value of the selected portion, an average value of the selected portion with at least one outlying value of the selected portion removed, a weighted average value of the selected portion, a median value of the selected portion, and/or the mode value of the selected portion, and/or combinations thereof.

7. The method of claim 1 further comprising:
   detecting, using the pulse oximeter, a second respiration rate event, wherein:
      the second respiration rate event is detected based at least in part on a second deviation in the respiration rate values; and
      the second respiration rate event precedes in time the first respiration rate event;
   determining, using the pulse oximeter, a second altered portion of the respiration rate values based on the second respiration rate event; and
   determining, using the pulse oximeter, the characteristic respiration rate of the patient based at least in part on another selected portion of the respiration rate values that excludes the first altered portion and the second altered portion of the respiration rate values.

8. The method of claim 1, wherein determining the characteristic respiration rate further comprises analyzing the oscillation of a portion of the PPG signal from which the selected portion of the respiration rate values that excludes the first altered portion of the respiration rate values is determined.

9. The method of claim 1, further comprising:
   transforming, using the pulse oximeter, a portion of the PPG signal from which the selected portion of the respiration rate values that excludes the first altered portion of the respiration rate values is determined into a transformed signal using a wavelet transform;
   generating, using the pulse oximeter, a scalogram based at least in part on the transformed signal;
   identifying, using the pulse oximeter, a band on the scalogram; extracting ridge information from the band;
   generating, using the pulse oximeter, at least one confidence measure based at least in part on the ridge information; and
   determining, using the pulse oximeter, the characteristic respiration rate based at least in part on the scalogram and the at least one confidence measure.

10. The method of claim 9, further comprising:
    selecting, using the pulse oximeter, a region of the scalogram;
    summing, using the pulse oximeter, amplitudes for each scale in the region;
    generating, using the pulse oximeter, the at least one confidence measure based at least in part on the ridge information and the summed amplitudes; and determining, using the pulse oximeter, the characteristic respiration rate based at least in part on the scalogram and the at least one confidence measure.

11. A system for determining a characteristic respiration rate of a patient, the system comprising:
  a pulse oximetry sensor configured to generate a photoplethysmographic (PPG) signal, wherein the pulse oximetry sensor is configured to detect light attenuated by the patient;
  a pulse oximeter coupled to the pulse oximetry sensor, wherein the pulse oximeter is configured to:
    determine respiration rate values of the patient over time based at least in part on the PPG signal;
    detect a first respiration rate event, wherein the first respiration rate event is detected based at least in part on a first deviation in the respiration rate values;
    determine a first altered portion of the respiration rate values based on the first respiration rate event; and
    determine the characteristic respiration rate of the patient based at least in part on a selected portion of the respiration rate values, wherein:
      the selected portion of the respiration rate values excludes the first altered portion of the respiration rate values;
      the selected portion of the respiration rate values occurs earlier in time than the first altered portion of the respiration rate values; and
      the characteristic respiration rate is not determined based on the first altered portion of the respiration rate values; and
  an output coupled to the pulse oximeter, wherein the output is configured to display the characteristic respiration rate.

12. The system of claim 11 wherein:
  the pulse oximeter is further configured to:
    determine blood pressure values over time based at least in part on the PPG signal, wherein a first blood pressure value is determined based at least in part on a first blood pressure event and wherein the first blood pressure event is detected based at least in part on a deviation in the blood pressure values;
    identify a relaxation time based at least in part on the blood pressure values, wherein the relaxation time occurs later in time than the first blood pressure event; and
    derive a characteristic blood pressure of the patient based at least in part on a blood pressure value at the relaxation time, wherein the characteristic blood pressure is continuously derived to assess the clinical status of the patient; and
  the output is further configured to display the characteristic blood pressure.

13. The system of claim 12, wherein the pulse oximeter is further configured to analyze at least one of the first blood pressure value, the characteristic blood pressure, and the relaxation time to assess the anxiety of the patient.

14. The system of claim 11 wherein the pulse oximeter is further configured to:
  define the selected portion of the respiration rate values as the portion of the respiration rate values that excludes the first altered portion of the respiration rate values; and
  determine the characteristic respiration rate based at least in part on the group consisting of an average value of the selected portion, an average value of the selected portion with at least one outlying value of the selected portion removed, a weighted average value of the selected portion, a median value of the selected portion, and/or the mode value of the selected portion, and/or combinations thereof.

15. The system of claim 11, wherein the pulse oximeter is further configured to:
  detect a second respiration rate event, wherein:
    the second respiration rate event is detected based at least in part on a second deviation in the respiration rate values; and
    the second respiration rate event precedes in time the first respiration rate event;
  determine a second altered portion of the respiration rate values based on the second respiration rate event; and
  determine the characteristic respiration rate of the patient based at least in part on another selected portion of the respiration rate values that excludes the first altered portion and the second altered portion of the respiration rate values.

16. The system of claim 11, wherein the pulse oximeter is further configured to determine the characteristic respiration rate based at least in part on the oscillation of a portion of the PPG signal from which the selected portion of the respiration rate values that excludes the first altered portion of the respiration rate values is determined.

17. The system of claim 11, wherein the pulse oximeter is further configured to:
  transform a portion of the PPG signal from which the selected portion of the respiration rate values that excludes the first altered portion of the respiration rate values is determined into a transformed signal using a wavelet transform;
  generate a scalogram based at least in part on the transformed signal;
  identify a band on the scalogram;
  extract ridge information from the band;
  generate at least one confidence measure based at least in part on the ridge information; and
  determine the characteristic respiration rate based at least in part on the scalogram and the at least one confidence measure.

18. The system of claim 17, wherein the pulse oximeter is further configured to:
  select a region of the scalogram;
  sum amplitudes for each scale in the region;
  generate the at least one confidence measure based at least in part on the ridge information and the summed amplitudes; and
  determine the characteristic respiration rate based at least in part on the scalogram and the at least one confidence measure.

19. A non-transitory computer-readable medium for use in determining a characteristic respiration rate of a patient, the computer-readable medium comprising:
  computer program instructions recorded thereon for causing a pulse oximeter to:
    receive a photoplethysmographic (PPG) signal derived from a pulse oximetry sensor, wherein the pulse oximetry sensor is configured to detect light attenuated by the patient;
    determine respiration rate values of the patient over time based at least in part on the PPG signal obtained from a patient sensor;
    detect a first respiration rate event, wherein the first respiration rate event is detected based at least in part on a deviation in the respiration rate values;
    detect a first altered portion of the respiration rate values based on the first respiration rate event;

determine the characteristic respiration rate of the patient based at least in part on a selected portion of the respiration rate values, wherein:
- the selected portion of the respiration rate values excludes the first altered portion of the respiration rate values;
- the selected portion of the respiration rate values occurs earlier in time than the first altered portion of the respiration rate values;
- the determining of the characteristic respiration rate is not based on the first altered portion of the respiration rate values; and
- the characteristic respiration rate is determined to assess a clinical status of the patient; and configure an output to display the characteristic respiration rate.

20. The non-transitory computer-readable medium of claim 19, further comprising computer program instructions recorded thereon for causing the pulse oximeter to:
- determine values over time based at least in part on the PPG signal obtained from the patient sensor, wherein:
  - a first blood pressure value is determined based at least in part on a first blood pressure event; and
  - the first blood pressure event is detected based at least in part on a deviation in the blood pressure values;
- identify a relaxation time based at least in part on the blood pressure values, wherein the relaxation time occurs later in time than the first blood pressure event; and
- derive a characteristic blood pressure of the patient based at least in part on a blood pressure value at a relaxation time, wherein the characteristic blood pressure is continuously derived to assess the clinical status of the patient.

* * * * *